United States Patent
Sohn et al.

(10) Patent No.: US 9,770,231 B2
(45) Date of Patent: Sep. 26, 2017

(54) PNEUMATIC MEDICAL MOTORS FOR A SURGICAL CONTROLLER

(71) Applicant: Rainbow Medical Ltd., Herzliya (IL)

(72) Inventors: Zev Sohn, Ginot Shomron (IL); Yossi Gross, Moshav Mazor (IL); Opher Kinrot, Ra'anana (IL)

(73) Assignee: RAINBOW MEDICAL LTD., Herzliya (IL)

( * ) Notice: Subject to any disclaimer, the term of this patent is extended or adjusted under 35 U.S.C. 154(b) by 397 days.

(21) Appl. No.: 14/439,783

(22) PCT Filed: Oct. 30, 2013

(86) PCT No.: PCT/IL2013/050887
§ 371 (c)(1),
(2) Date: Apr. 30, 2015

(87) PCT Pub. No.: WO2014/068563
PCT Pub. Date: May 8, 2014

(65) Prior Publication Data
US 2015/0297203 A1    Oct. 22, 2015

Related U.S. Application Data

(60) Provisional application No. 61/838,662, filed on Jun. 24, 2013, provisional application No. 61/767,885, (Continued)

(30) Foreign Application Priority Data

Oct. 30, 2012    (GB) .................................. 1219491.6

(51) Int. Cl.
*A61B 17/00*    (2006.01)
*A61B 17/17*    (2006.01)
(Continued)

(52) U.S. Cl.
CPC ........ *A61B 17/00234* (2013.01); *A61B 17/00* (2013.01); *A61B 17/17* (2013.01);
(Continued)

(58) Field of Classification Search
CPC .............. A61B 17/00; A61B 17/00234; A61B 17/0218; A61B 17/1628; A61B 17/17;
(Continued)

(56) References Cited

U.S. PATENT DOCUMENTS 2,884,852 A    5/1959    Saltz
5,503,631 A    4/1996    Onishi et al.
(Continued)

FOREIGN PATENT DOCUMENTS

WO    WO2014068563    5/2014

OTHER PUBLICATIONS

An International Search Report and Written Opinion issued on Apr. 9, 2014 in PCT/IL2013/050887.
(Continued)

*Primary Examiner* — Logan Kraft
(74) *Attorney, Agent, or Firm* — Sughrue Mion, PLLC

(57) ABSTRACT

Apparatus is provided, comprising first and second rails (140) and a pneumatic motor assembly (22). The assembly comprises a first motor subassembly (180), comprising a first-motor subassembly locking balloon (160), which locks the first rail to the first motor subassembly by inflation thereof; and a first-motor subassembly moving balloon (170), which moves the first rail by a mechanism of either inflation or deflation of the first-motor subassembly moving balloon, when the first-motor locking balloon is inflated. Assembly (22) additionally comprises a second motor subassembly (185), comprising a second-motor assembly locking balloon (165), which locks the second rail to the second motor subassembly by inflation thereof; and a second-motor
(Continued)

subassembly moving balloon (175), configured to move the second rail by a mechanism selected from either inflation or deflation of the second-motor subassembly moving balloon, when the second-motor subassembly locking balloon is inflated. Other applications are also provided.

23 Claims, 29 Drawing Sheets

Related U.S. Application Data filed on Feb. 22, 2013, provisional application No. 61/722,328, filed on Nov. 5, 2012.

(51) Int. Cl.
| | | |
|---|---|---|
| *A61B 90/57* | (2016.01) | |
| *A61B 90/00* | (2016.01) | |
| *A61B 17/16* | (2006.01) | |
| *A61B 17/02* | (2006.01) | |
| *A61B 17/32* | (2006.01) | |
| *A61B 90/50* | (2016.01) | |
| *A61B 34/30* | (2016.01) | |

(52) U.S. Cl.
CPC .............. *A61B 90/00* (2016.02); *A61B 90/57* (2016.02); *A61B 17/0218* (2013.01); *A61B 17/1628* (2013.01); *A61B 17/320016* (2013.01); *A61B 34/30* (2016.02); *A61B 90/37* (2016.02); *A61B 90/50* (2016.02); *A61B 2017/00203* (2013.01); *A61B 2017/00216* (2013.01); *A61B 2017/00296* (2013.01); *A61B 2017/00398* (2013.01); *A61B 2017/00544* (2013.01)

(58) Field of Classification Search
CPC ........... A61B 2017/00203; A61B 2017/00216; A61B 2017/00296; A61B 2017/00398; A61B 2017/00544; A61B 2017/22051; A61B 2017/320016; A61B 34/30; A61B 90/00; A61B 90/37; A61B 90/50; A61B 90/57

See application file for complete search history.

(56) References Cited

U.S. PATENT DOCUMENTS

| | | | |
|---|---|---|---|
| 5,662,587 | A | 9/1997 | Grundfest et al. |
| 6,149,660 | A | 11/2000 | Laufer et al. |
| 8,182,476 | B2 | 5/2012 | Julian et al. |
| 2003/0036727 | A1 | 2/2003 | Schock |
| 2003/0069523 | A1 | 4/2003 | Williams et al. |
| 2005/0070950 | A1 | 3/2005 | Mason et al. |
| 2008/0091073 | A1 | 4/2008 | Park |
| 2009/0091066 | A1 | 4/2009 | Sleva et al. |
| 2009/0131752 | A1 | 5/2009 | Park |
| 2010/0022947 | A1 | 1/2010 | Hassidov et al. |
| 2010/0135563 | A1 | 6/2010 | Kelly et al. |
| 2010/0191220 | A1 | 7/2010 | Webler et al. |
| 2011/0190583 | A1* | 8/2011 | Ashida ................... A61B 1/00 600/115 |

OTHER PUBLICATIONS

An International Preliminary Report on Patentability and Written Opinion issued on May 5, 2015 in PCT/IL2013/050887.

"Outer Shell Actuator Driving Central Bending Shaft by Balloon Arrays Circumferentially-Arranged Inside of Shell" Konishi Lab, Micro/Nano Mechatronics LAB.

* cited by examiner

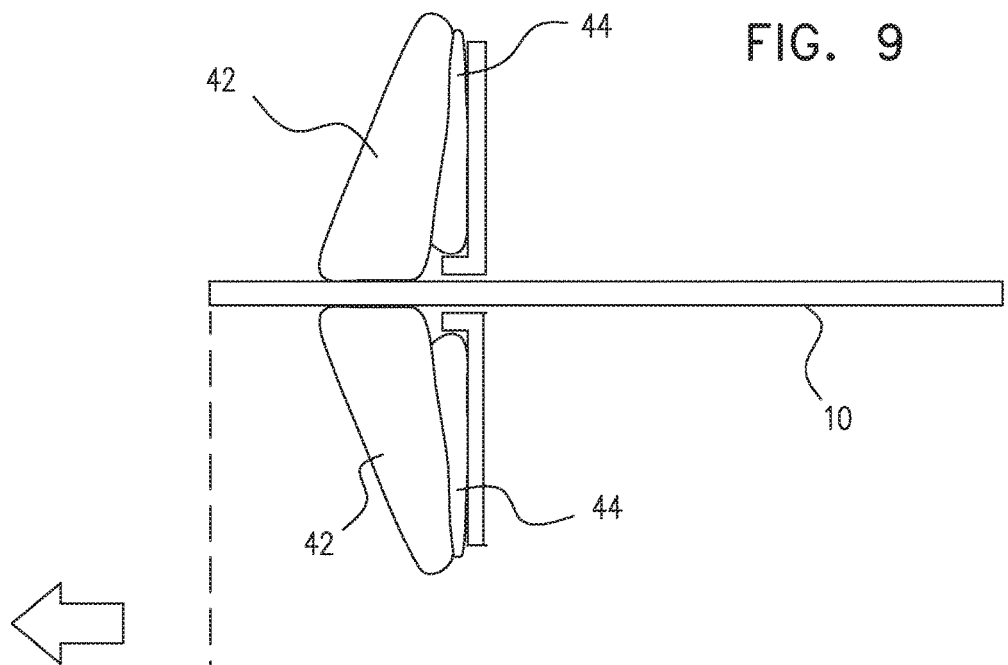
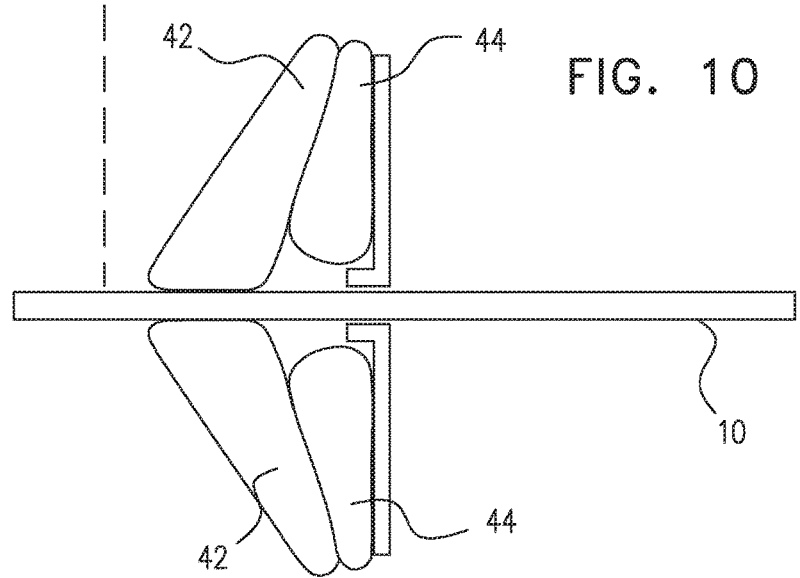

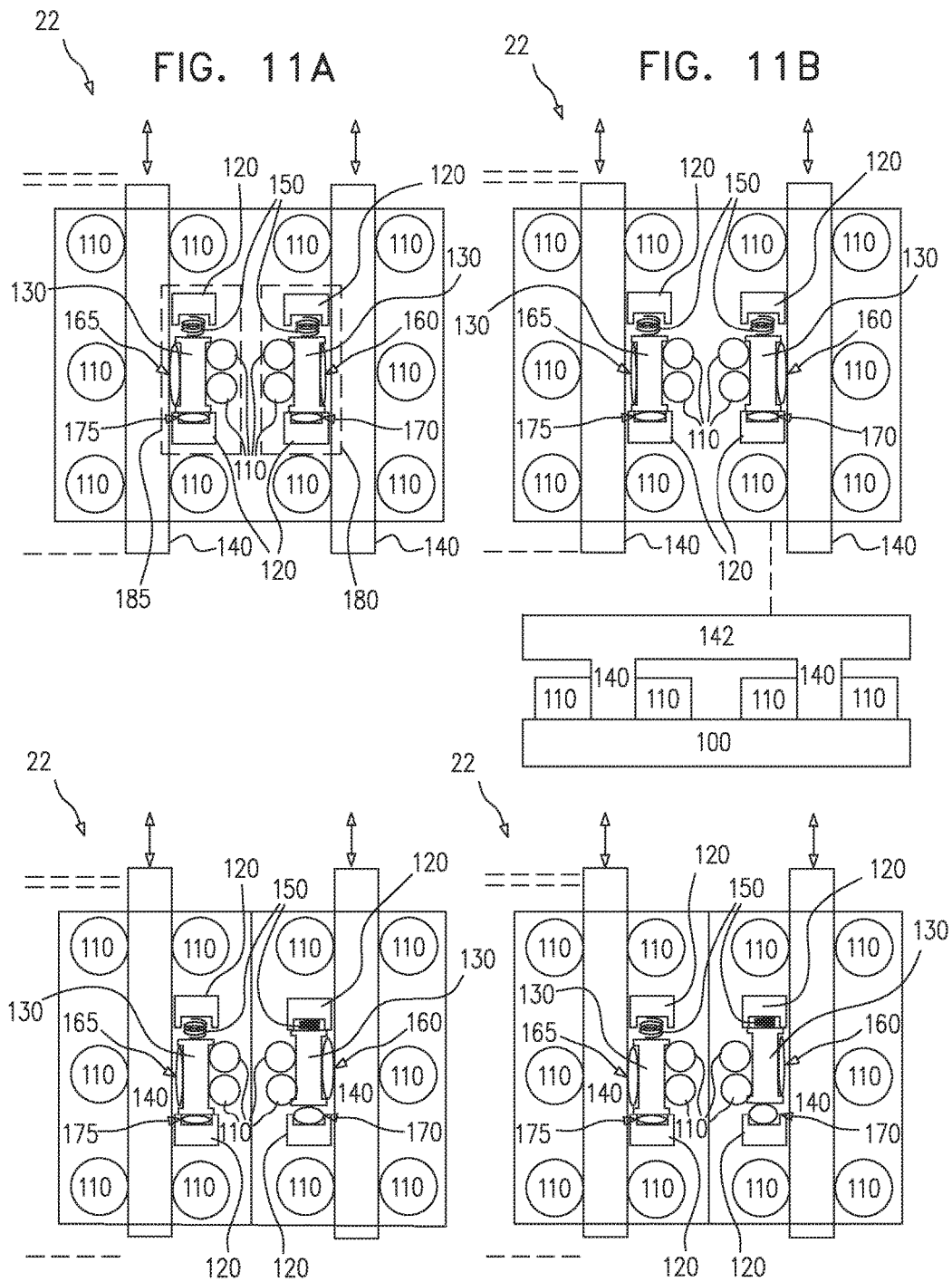

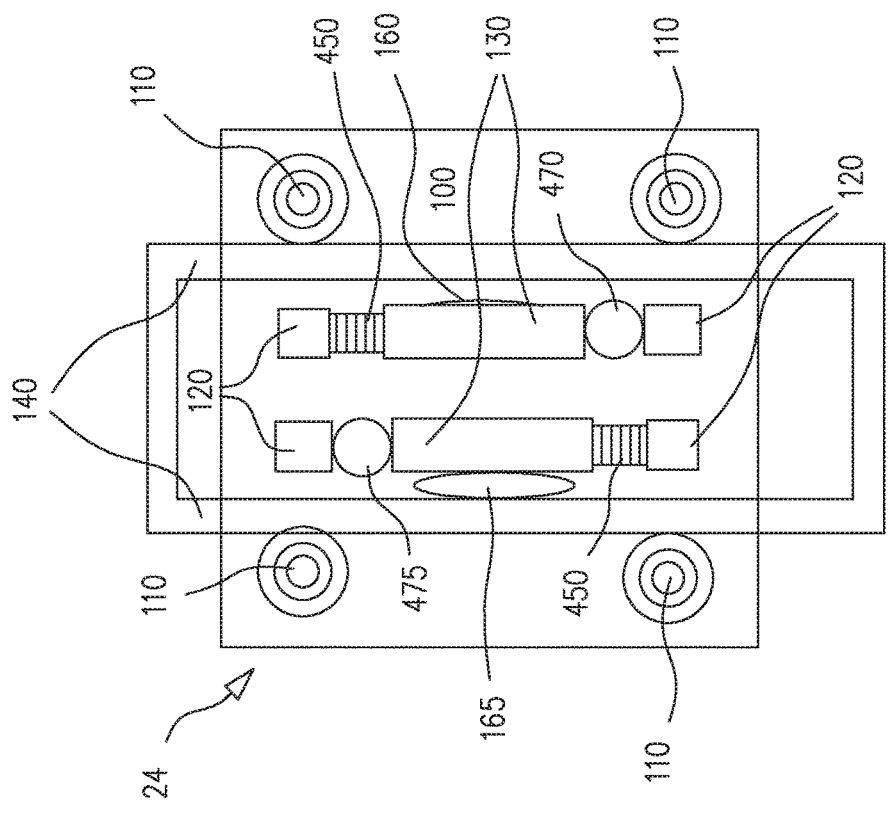
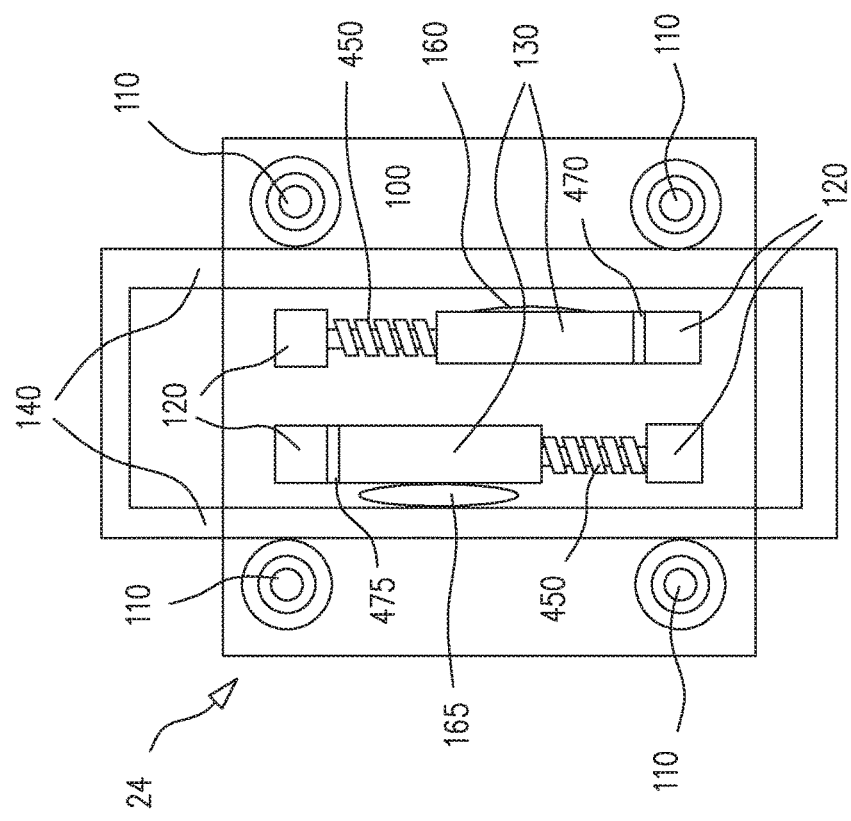

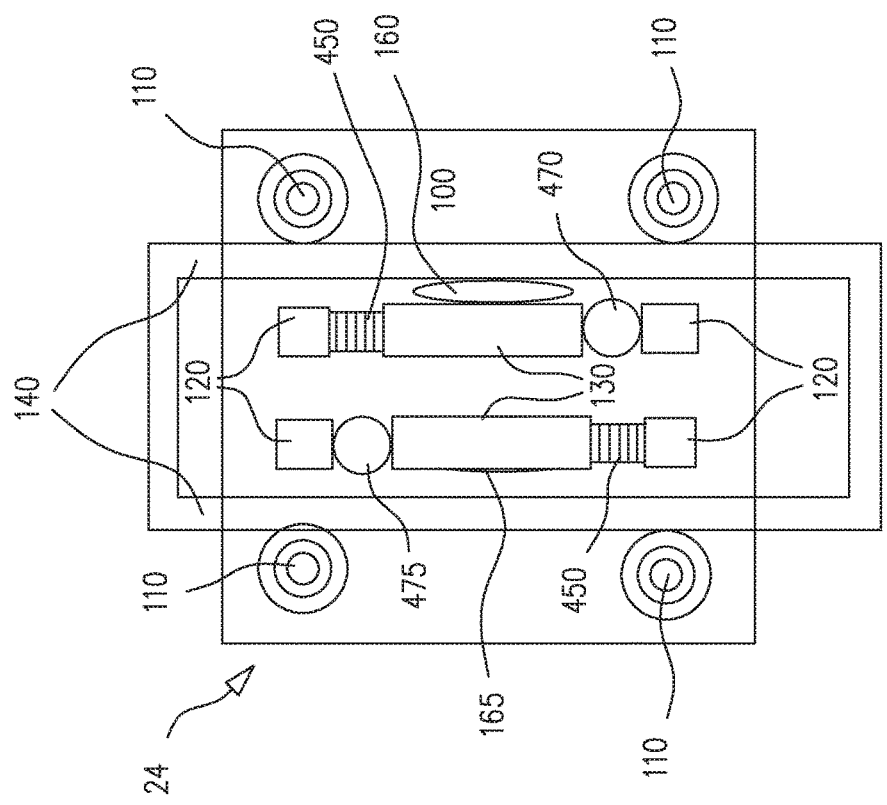
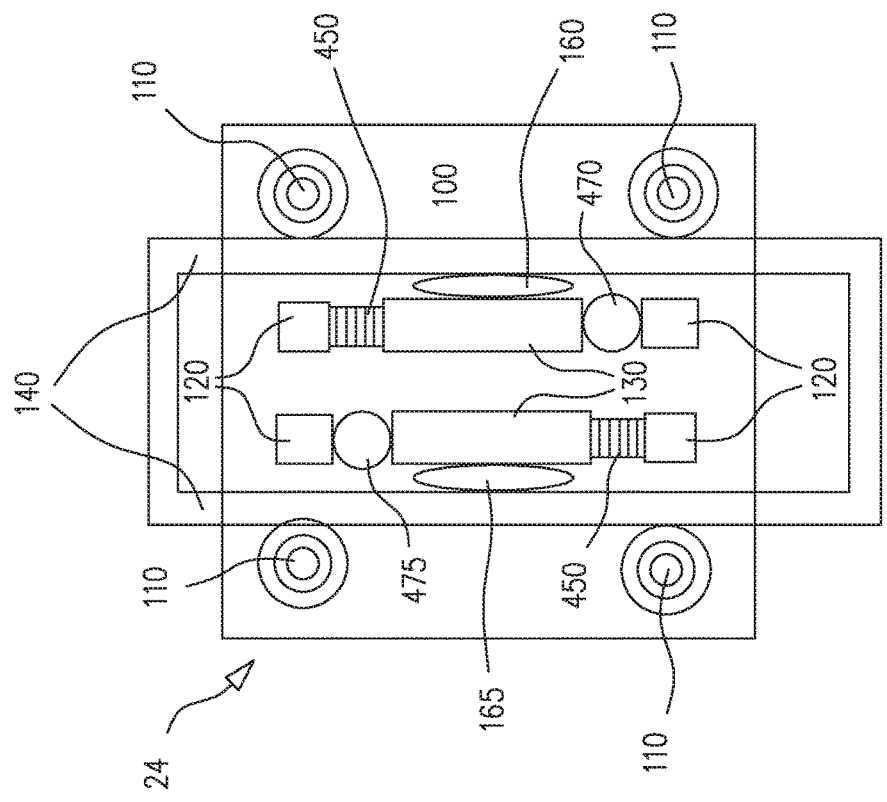

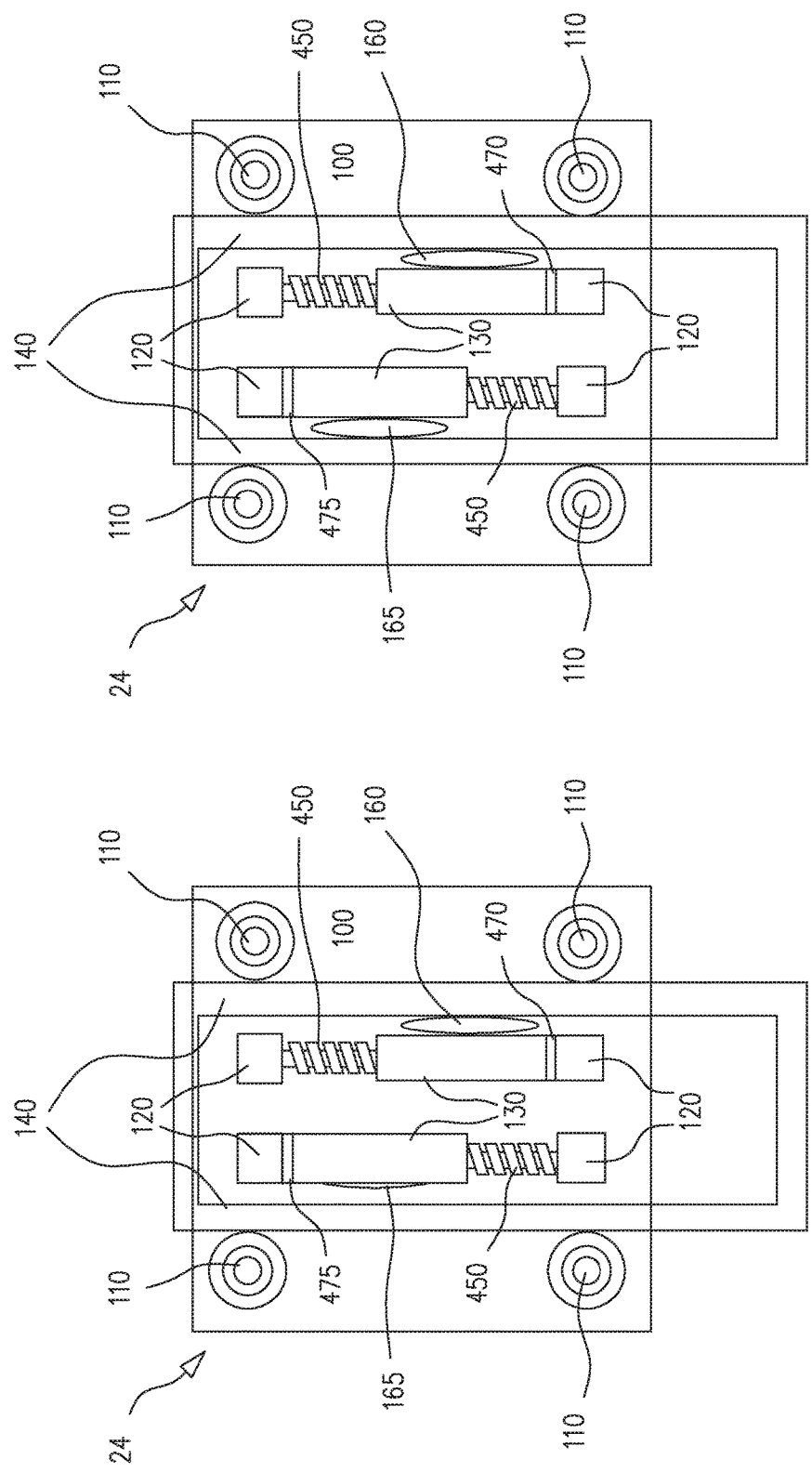

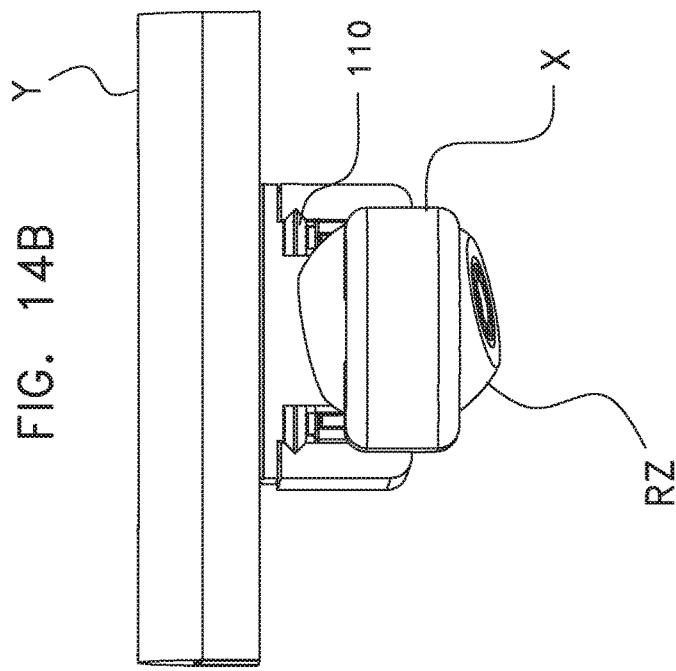
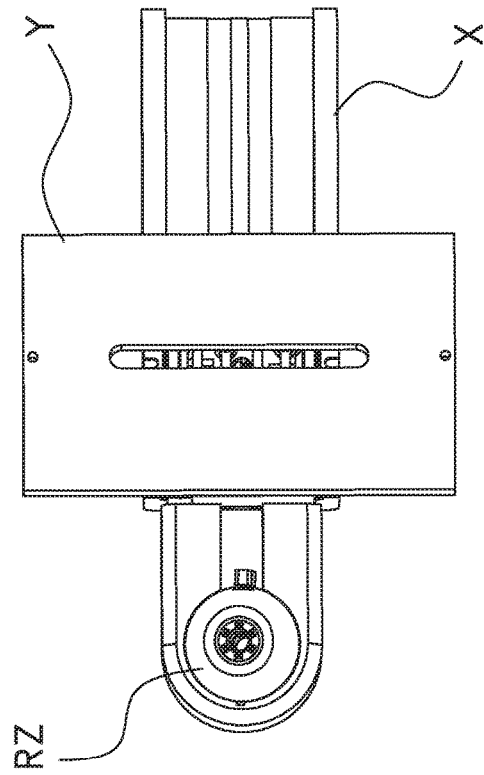

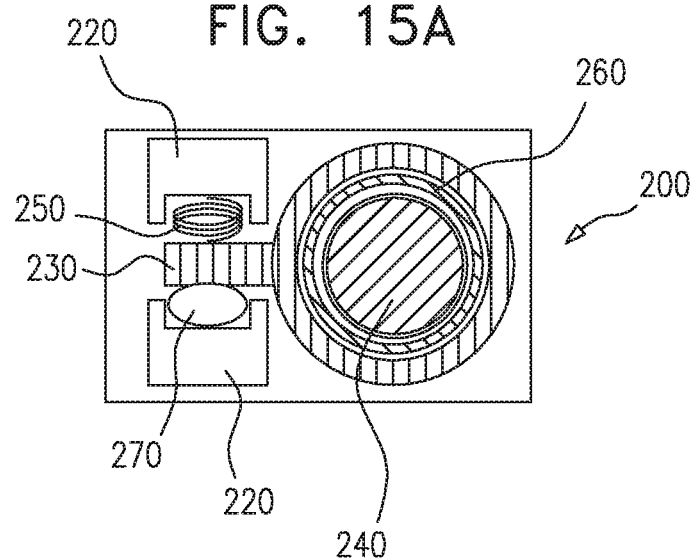
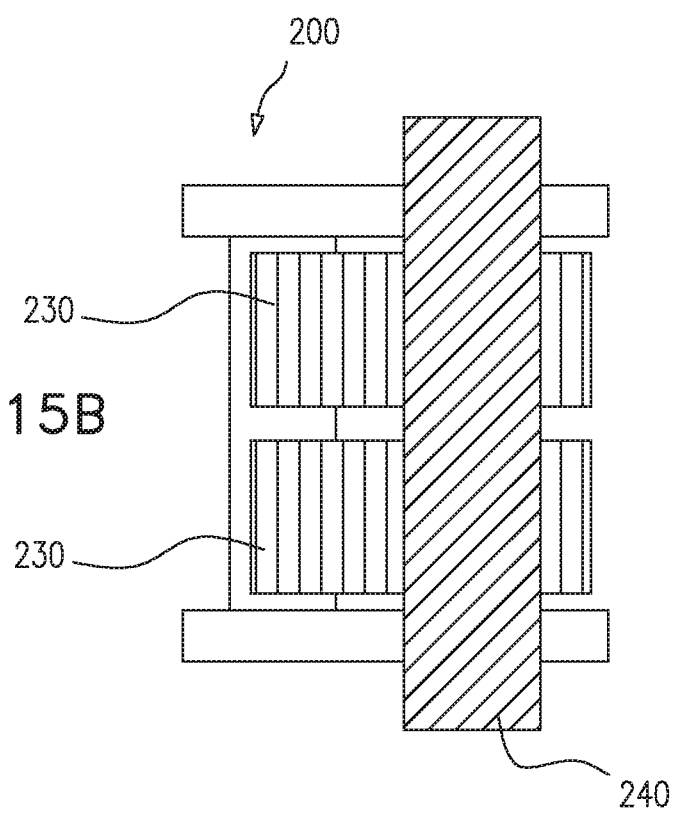

PNEUMATIC MEDICAL MOTORS FOR A SURGICAL CONTROLLER

CROSS-REFERENCES TO RELATED APPLICATIONS

The present application claims the priority of:

U.S. Provisional Patent Application No. 61/838,662, entitled "Pneumatic Medical Motors," filed Jun. 24, 2013;

U.S. Provisional Patent Application No. 61/767,885, entitled "Pneumatic Medical Motors," filed Feb. 22, 2013;

U.S. Provisional Patent Application No. 61/722,328, entitled "Surgical Controller," filed Nov. 5, 2012; and UK Patent Application No. 1219491.6, entitled "Surgical Controller," filed Oct. 30, 2012.

All of the above-mentioned applications are incorporated herein by reference.

FIELD OF THE APPLICATION

Applications of the present invention relate generally to surgical control apparatus, and particularly to pneumatic motors for surgical control and assisting laparoscopic surgical procedures.

BACKGROUND OF THE APPLICATION

Laparoscopic surgery is a type of minimally-invasive surgery typically performed through small incisions in the abdomen. Laparoscopic surgery is associated with many ergonomic challenges and therefore there are continuous efforts to improve the ergonomics of laparoscopic surgery.

Minimally-invasive surgical procedures have been augmented by technological developments designed to improve the efficiency and outcome of these procedures. For example, laparoscopic surgery may be aided by surgical robots, whereby a surgeon operates the robot from a nearby console or from a remote location. Some of the advantages of robotically-assisted minimally-invasive surgery are precision and improved tool manipulation. Robotic surgery typically utilizes a motor mechanism that manipulates and provides precision control over the surgical tool.

SUMMARY OF APPLICATIONS

In accordance with applications of the present invention, surgical-control apparatus having a pneumatic motor assembly is provided for assisting a Minimally-Invasive Surgery (MIS) procedure on a patient, e.g., laparoscopic surgery. Typically, the apparatus is fully controlled by a surgeon and is configured to manipulate one or more laparoscopic tools during surgery, in accordance with the surgeon's needs. The laparoscopic tools typically comprise a laparoscope and additional specialized instruments which are introduced into the body of the patient during laparoscopic surgical procedures, e.g., an organ retractor or a cutting tool.

Generally, the pneumatic motor assembly comprises one or more inflatable components (e.g., balloons) configured to control a disposition of the laparoscopic tool within the patient by inflation and deflation of the inflatable components located in the surgical-control apparatus.

The principles of pneumatic motion can be used, in accordance with applications of the present invention, for control of a tool shaft, as well as for pneumatic remote control of laparoscopic tools, e.g., closing and opening a tool handle with a controlled motion range and force.

For some applications, the surgical-control apparatus comprises a pneumatic motor that moves a linear or curved slide that is configured to control a disposition of the laparoscopic tool within the patient. In accordance with some applications of the present invention, the surgical-control apparatus comprises a pneumatic motor comprising first and second rails and a pneumatic motor assembly comprising first and second motor subassemblies.

The first motor subassembly typically comprises a first-motor subassembly locking balloon which locks the first rail to the first motor subassembly by inflation of the first-motor subassembly locking balloon. The first motor subassembly additionally comprises a first-motor subassembly moving balloon, which moves the first rail (along with the second rail) by a mechanism of either a) inflation of the first-motor subassembly moving balloon, when the first-motor subassembly locking balloon is inflated, or b) deflation of the first-motor subassembly moving balloon, when the first-motor subassembly locking balloon is inflated.

The second motor subassembly typically comprises a second-motor subassembly locking balloon which locks the second rail to the second motor subassembly by inflation of the second-motor subassembly locking balloon. The second motor subassembly additionally comprises a second-motor subassembly moving balloon, which moves the second rail (along with the first rail) by a mechanism of either a) inflation of the second-motor subassembly moving balloon, when the second-motor subassembly locking balloon is inflated, and b) deflation of the second-motor subassembly moving balloon, when the second-motor subassembly locking balloon is inflated.

Additional pneumatic motor mechanisms for pneumatic remote control of surgical tools are described.

There is therefore provided in accordance with some applications of the present invention, a surgical pneumatic motor apparatus, including:

first and second rails; and a pneumatic motor assembly, including:

a first motor subassembly, including:

a first-motor subassembly locking balloon, configured to lock the first rail to the first motor subassembly by inflation of the first-motor subassembly locking balloon; and a first-motor subassembly moving balloon, configured to move the first rail by a mechanism selected from the group consisting of:

a) inflation of the first-motor subassembly moving balloon, when the first-motor subassembly locking balloon is inflated, and b) deflation of the first-motor subassembly moving balloon, when the first-motor subassembly locking balloon is inflated; and a second motor subassembly, including:

a second-motor subassembly locking balloon, configured to lock the second rail to the second motor subassembly by inflation of the second-motor subassembly locking balloon; and a second-motor subassembly moving balloon, configured to move the second rail by a mechanism selected from the group consisting of:

a) inflation of the second-motor subassembly moving balloon, when the second-motor subassembly locking balloon is inflated, and b) deflation of the second-motor subassembly moving balloon, when the second-motor subassembly locking balloon is inflated.

For some applications:
the first motor subassembly further includes a first-motor subassembly spring, configured to oppose motion induced by inflation of the first-motor subassembly moving balloon, and
the second motor subassembly further includes a second-motor subassembly spring, configured to oppose motion induced by inflation of the second-motor subassembly moving balloon.

For some applications, the first-motor subassembly moving balloon is configured to move the first rail in a first direction by inflation of the first-motor subassembly moving balloon, when the first-motor subassembly locking balloon is inflated, and the second-motor subassembly moving balloon is configured to move the second rail in the first direction by deflation of the second-motor subassembly moving balloon, when the second-motor subassembly locking balloon is inflated.

For some applications, the first-motor subassembly moving balloon is configured to move the first rail in a first direction by inflation of the first-motor subassembly moving balloon, when the first-motor subassembly locking balloon is inflated, and the second-motor subassembly moving balloon is configured to move the second rail in the first direction by inflation of the second-motor subassembly moving balloon, when the second-motor subassembly locking balloon is inflated.

For some applications:
the first motor subassembly further includes a first-motor subassembly locking element,
the first-motor subassembly locking balloon is configured to lock the first rail to the first motor subassembly by pushing the first-motor subassembly locking element against the first rail,
the second motor subassembly further includes a second-motor subassembly locking element, and
the second-motor subassembly locking balloon is configured to lock the second rail to the second motor subassembly by pushing the second-motor subassembly locking element against the second rail.

For some applications, the apparatus further including a first and a second motor subassembly spring positioned to compress the first-motor subassembly locking balloon and second-motor subassembly locking balloon, respectively, by applying respective forces to the first-motor subassembly locking element and to the second-motor subassembly locking element.

For some applications, the first motor subassembly is shaped to define a restricting wall, configured to only allow motion of the first-motor subassembly locking element that is toward the first rail or away from the first rail.

For some applications, the second motor subassembly is shaped to define a restricting wall, configured to only allow motion of the second-motor subassembly locking element that is toward the second rail or away from the second rail.

For some applications, the first-motor subassembly locking element is configured to prevent inflation of the first-motor subassembly locking balloon to a maximum inflation volume thereof, and
the second-motor subassembly locking element is configured to prevent inflation of the second-motor subassembly locking balloon to a maximum inflation volume thereof.

For some applications, the apparatus being for use with a pressure source, the apparatus further including:
one or more tubes coupled to the pressure source and configured to facilitate propagation of air from the pressure source to the motor assembly; and
one or more control valves configured to control air pressure in the one or more tubes.

For some applications, the first-motor subassembly locking balloon is configured to lock the first rail to the first motor subassembly by applying a force of 5-15 kgF.

For some applications, at least one of the one or more tubes has a length of 0.1-3 meters.

For some applications, the at least one of the one or more tubes has a length of 0.4-1.5 meters.

For some applications, at least one of the one or more tubes has a cross-sectional area of 0.5-1.5 mm2.

For some applications, at least one of the one or more tubes has an inner diameter of 0.8-1.4 mm.

For some applications, at least one of the one or more tubes has an external diameter of 1.3-2 mm.

For some applications, at least one of the one or more tubes has a wall thickness of 0.15-0.45 mm.

For some applications, the subassembly locking balloons each have a volume of 10-200 mm3 when fully inflated.

For some applications, the first-motor subassembly moving balloon and the second-motor subassembly moving balloon are configured to move the first and second rails during motion steps having a time duration of 10-30 ms.

For some applications, the first-motor subassembly moving balloon and the second-motor subassembly moving balloon are configured to move the first and second rails by 0.1-1 mm during respective motion steps.

For some applications, the first-motor subassembly locking balloon and the second-motor subassembly locking balloon each has a wall thickness of 0.05 mm to 0.15 mm.

For some applications, the first-motor subassembly locking balloon and the second-motor subassembly locking balloon each has a wall thickness of 0.08-0.12 mm.

For some applications, the first-motor subassembly moving balloon and the second-motor subassembly moving balloon each has a wall thickness of 0.05 mm to 0.15 mm.

For some applications, the first-motor subassembly moving balloon and the second-motor subassembly moving balloon each has a wall thickness of 0.08 to 0.12 mm.

There is additionally provided in accordance with some applications of the present invention a surgical apparatus, including:
a rail; and
a pneumatic motor, including:
a locking element;
a locking balloon, configured to lock the rail to the motor by pushing the locking element against the rail; and
a moving balloon, configured to move the rail by a mechanism selected from the group consisting of:
a) inflation of the moving balloon, when the locking balloon is inflated, and
b) deflation of the moving balloon, when the locking balloon is inflated.

For some applications, the locking element and locking balloon are separate components, and a surface contact area of the locking balloon and the locking element changes during inflation of the locking balloon.

There is further yet provided in accordance with some applications of the present invention a surgical pneumatic motor apparatus for use with a shaft, including:
a pneumatic motor assembly, including:
a first motor subassembly, including:
a first-motor subassembly locking balloon, configured to lock the shaft to the first motor subassembly by inflation of the first-motor subassembly locking balloon; and a first-motor subassembly moving balloon, configured to move the shaft by a mechanism selected from the group consisting of:
  a) inflation of the first-motor subassembly moving balloon, when the first-motor subassembly locking balloon is inflated, and
  b) deflation of the first-motor subassembly moving balloon, when the first-motor subassembly locking balloon is inflated; and a second motor subassembly, including:
  a second-motor subassembly locking balloon, configured to lock the shaft to the second motor subassembly by inflation of the second-motor subassembly locking balloon; and
  a second-motor subassembly moving balloon, configured to move the shaft by a mechanism selected from the group consisting of:
    a) inflation of the second-motor subassembly moving balloon, when the second-motor subassembly locking balloon is inflated, and
    b) deflation of the second-motor subassembly moving balloon, when the second-motor subassembly locking balloon is inflated.

For some applications, the first-motor subassembly moving balloon and the second-motor subassembly moving balloon are configured to move the shaft by moving the shaft along a longitudinal axis thereof.

For some applications, the first-motor subassembly moving balloon is configured to move the shaft in a first direction by inflation of the first-motor subassembly moving balloon, when the first-motor subassembly locking balloon is inflated, and the second-motor subassembly moving balloon is configured to move the shaft in the first direction by deflation of the second-motor subassembly moving balloon, when the second-motor subassembly locking balloon is inflated.

For some applications, the first-motor subassembly moving balloon is configured to move the shaft in a first direction by inflation of the first-motor subassembly moving balloon, when the first-motor subassembly locking balloon is inflated, and the second-motor subassembly moving balloon is configured to move the shaft in the first direction by inflation of the second-motor subassembly moving balloon, when the second-motor subassembly locking balloon is inflated.

For some applications, the first motor further includes a first-motor subassembly locking element,
  the first-motor subassembly locking balloon is configured to lock the shaft to the first motor by pushing the first-motor subassembly locking element against the shaft,
  the second motor subassembly further includes a second-motor subassembly locking element, and
  the second-motor subassembly locking balloon is configured to lock the shaft to the second motor subassembly by pushing the second-motor locking element against the shaft.

For some applications, the first motor subassembly further includes a first-motor subassembly spring, configured to oppose motion induced by inflation of the first-motor subassembly moving balloon, and
the second motor subassembly further includes a second-motor subassembly spring, configured to oppose motion induced by inflation of the second-motor subassembly moving balloon.

For some applications, the first-motor subassembly moving balloon and the second-motor subassembly moving balloon are configured to move the shaft by rotation of the shaft.

For some applications, the first-motor subassembly locking balloon is configured to surround the shaft, and the second-motor subassembly locking balloon is configured to surround the shaft.

There is still provided in accordance with some applications of the present invention, apparatus for assisting a minimally-invasive surgical procedure on a patient, the apparatus including:
  a first element configured to surround a first portion of a laparoscopic tool and to be coupled to a laparoscopic tool support arm, such that the laparoscopic tool is coupled to the laparoscopic tool support arm via the first element; and
  a second element configured to surround a second portion of the laparoscopic tool,
  the first element includes an actuator unit that is configured to control a disposition of the laparoscopic tool within the patient by changing a relative position of the second element with respect to the first element.

For some applications, the actuator unit includes inflatable components configured, in an inflated state thereof, to apply pressure to the first portion of the tool to manipulate the tool.

For some applications, the actuator unit includes inflatable components configured, in an inflated state thereof, to apply pressure to the second portion of the tool to manipulate the tool.

The present invention will be more fully understood from the following detailed description of embodiments thereof, taken together with the drawings, in which:

BRIEF DESCRIPTION OF THE DRAWINGS

FIGS. 9 and 10 are schematic illustrations of inflatable components in an actuator unit of the apparatus for assisting a minimally-invasive surgical procedure, in accordance with some applications of the present invention;

FIGS. 11A-H are schematic illustrations of a mechanism for a linear slide, in accordance with some applications of the present invention;

FIGS. 13A-F are schematic illustrations of a mechanism for a linear slide, in accordance with some applications of the present invention;

FIGS. 14A-B are schematic illustrations of combined slides in an orthogonal configuration, along with combined pneumatic push/pull and rotation control for surgical tool shaft manipulation, in accordance with some applications of the present invention;

FIGS. 15A-B are schematic illustrations of two cross-sections of a motor assembly, in accordance with some applications of the present invention;

DETAILED DESCRIPTION OF APPLICATIONS

Figure 1:
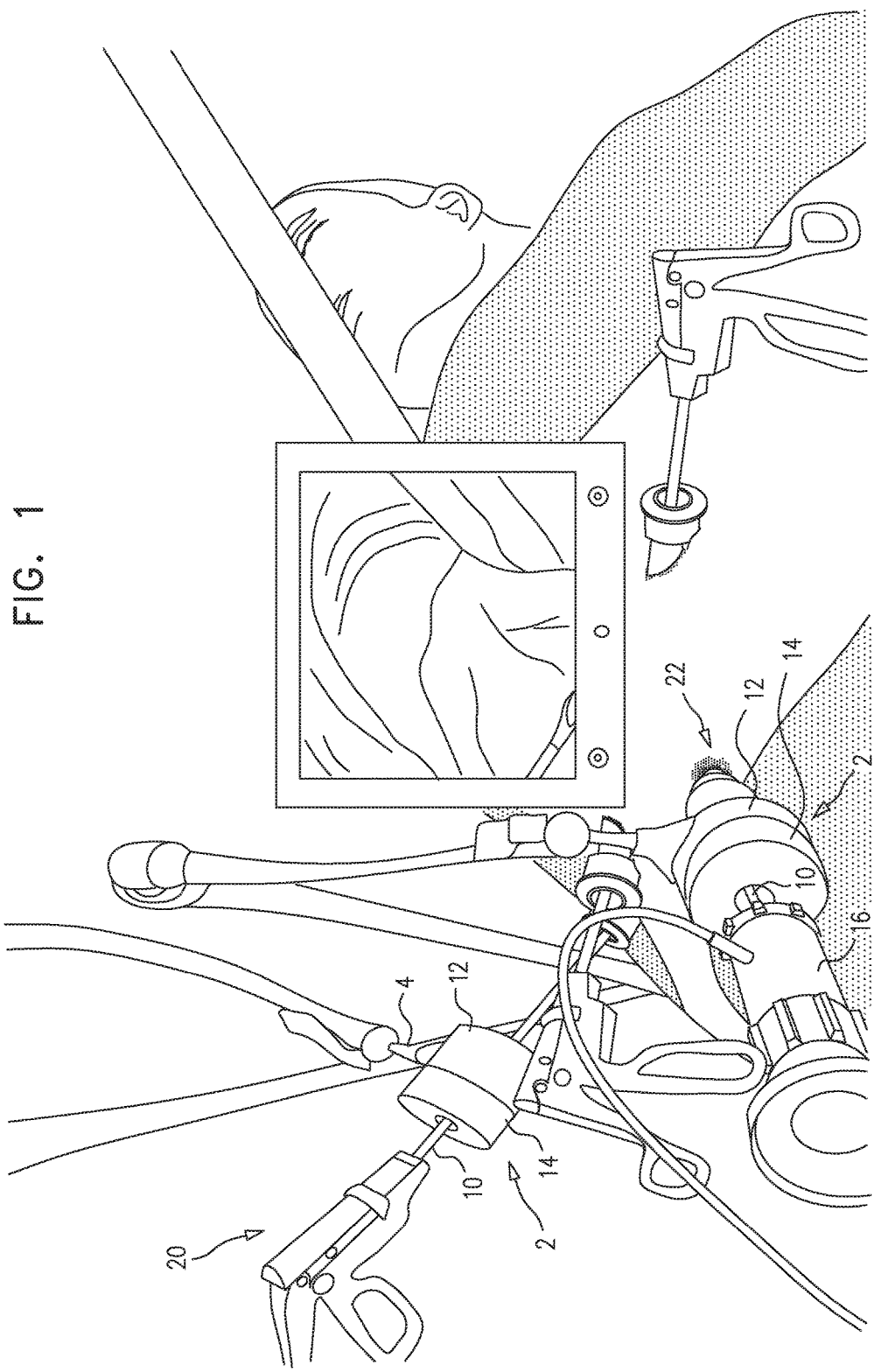
FIG. 1 is a schematic illustration of apparatus for assisting a minimally-invasive surgical procedure by remote control of a laparoscope and surgical tools by two pneumatically-driven robotic mechanisms, in accordance with some applications of the present invention.

Reference is made to FIG. 1, which is a schematic illustration of surgical-control apparatus 2 for assisting a minimally-invasive surgical procedure. For some applications, the apparatus, or components thereof, are mounted onto a portion of the laparoscopic tool to control manipulation of the tool, such that the operating surgeon does not directly move the tool.

Apparatus 2 is shown coupled to laparoscopic tools 20 and 22 in an operating room setup, in accordance with some applications of the present invention. FIG. 1 shows two units of apparatus 2, by way of illustration and not limitation. It is noted that any suitable number of apparatus 2 may be used, e.g., 1 or 3 or more, in accordance with the number of surgical tools used in during the surgical procedure. As shown, each apparatus 2 is coupled to a laparoscopic tool during the laparoscopic surgery. Each apparatus 2 comprises a first element 12 and a second element 14. Elements 12 and 14 are typically configured to generally surround portions of laparoscopic tools 20 and 22, e.g., shaft 10 of tools 20 and 22. Element 12 is typically coupled to support arms 4 of laparoscopic tools 20 and 22, such that laparoscopic tools 20 and 22 are coupled to support arms 4 via first element 12. Support arms 4 are typically jointed support arms. Typically, apparatus 2 comprises pneumatically-driven robotic mechanisms and elements 12 and 14 include inflatable elements therein.

Figure 2:
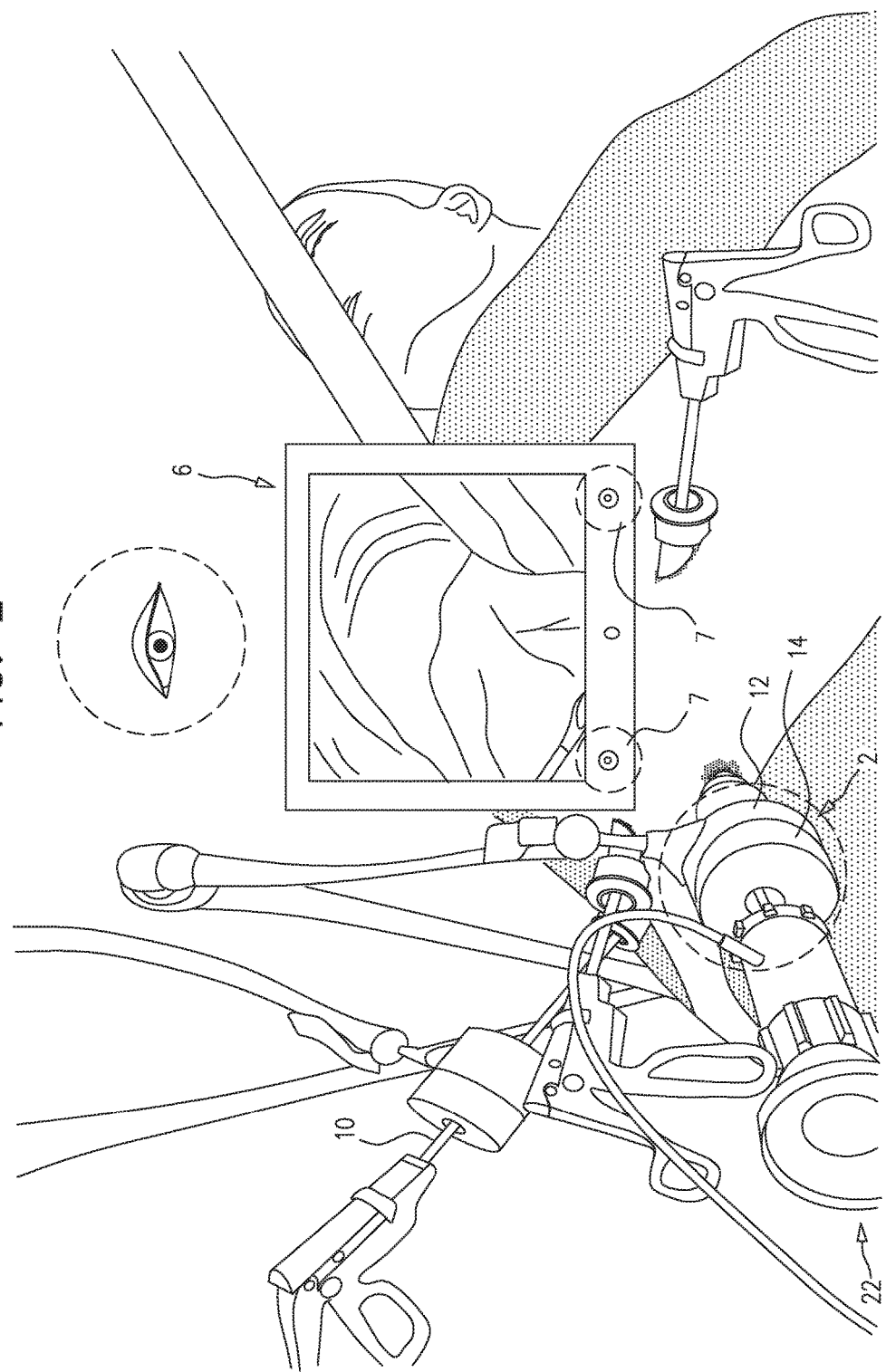
FIG. 2 is a schematic illustration of an eye-tracking system for use with the apparatus of FIG. 1, in accordance with some applications of the present invention.

Reference is made to FIG. 2, which is a schematic illustration of two units of apparatus 2 coupled to laparoscopic tools 20 and 22 during a laparoscopic procedure, in accordance with some applications of the present invention. For some applications, apparatus 2 is configured for use with an eye-tracking system comprising a high definition two-dimensional or three-dimensional display 6. For some applications, the display comprises a three-dimensional autostereoscopic display for use with a three-dimensional imaging laparoscopic camera.

As shown in FIG. 2, apparatus 2 is coupled to shaft 10 of laparoscopic tool 22 which comprises a laparoscope. The laparoscope is inserted into the patient's body, and display 6 presents a two-dimensional or three-dimensional image of the patient's internal organs. The eye-tracking system typically comprises one or more eye-tracking sensors 7 configured to follow the surgeon's gaze and in response change a disposition of second element 14, such that tool 22 is manipulated. As a result, the laparoscope is moved and the image is (for example) centered on the object of the surgeon's gaze. As described hereinbelow, for some applications, the eye tracking system additionally controls articulation of the surgical tools in response to the surgeon's gaze.

Figure 3:
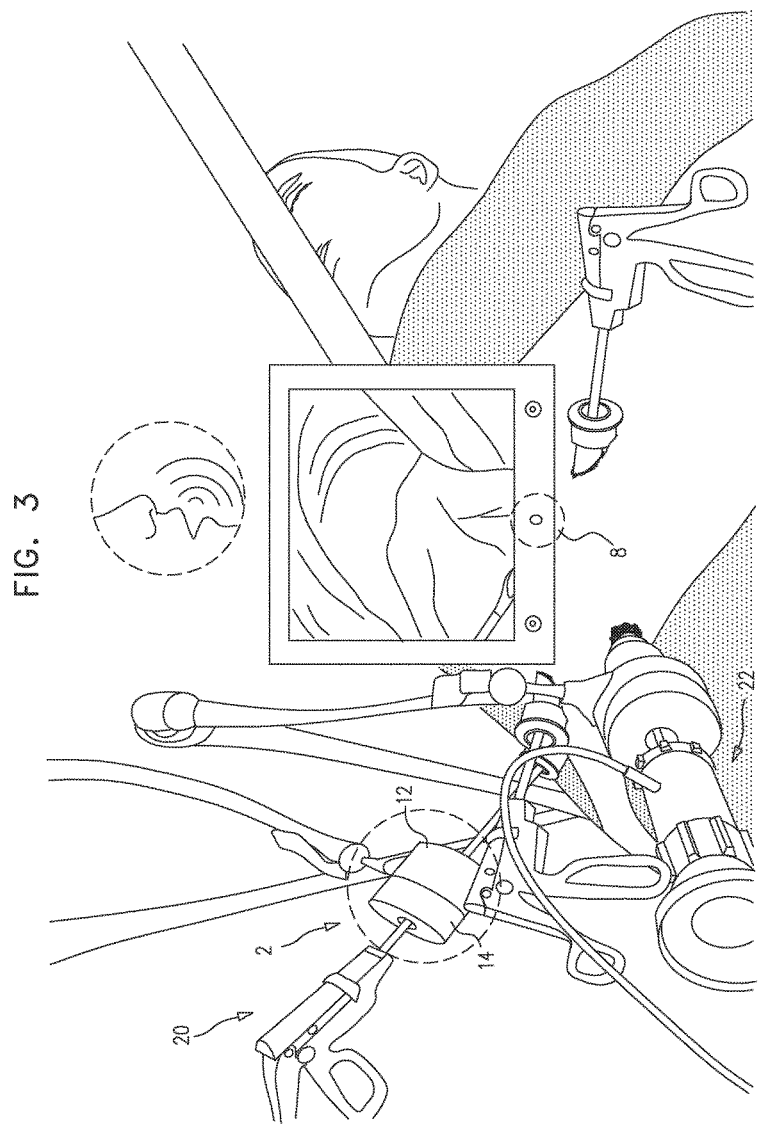
FIG. 3 is a schematic illustration of a voice control system for use with the apparatus of FIG. 1, in accordance with some applications of the present invention.

Reference is made to FIG. 3, which is a schematic illustration of an operating surgeon controlling apparatus 2 by audio (e.g., voice) control, in accordance with some applications of the present invention. For such applications, high definition display 6 (or another portion of the apparatus) comprises a microphone 8 which receives voice commands from the surgeon, resulting in re-positioning of the laparoscope and/or the other surgical tools. By operating apparatus 2 in this manner the surgeon can control zoom, translation, or rotation of the laparoscope.

Figure 4:
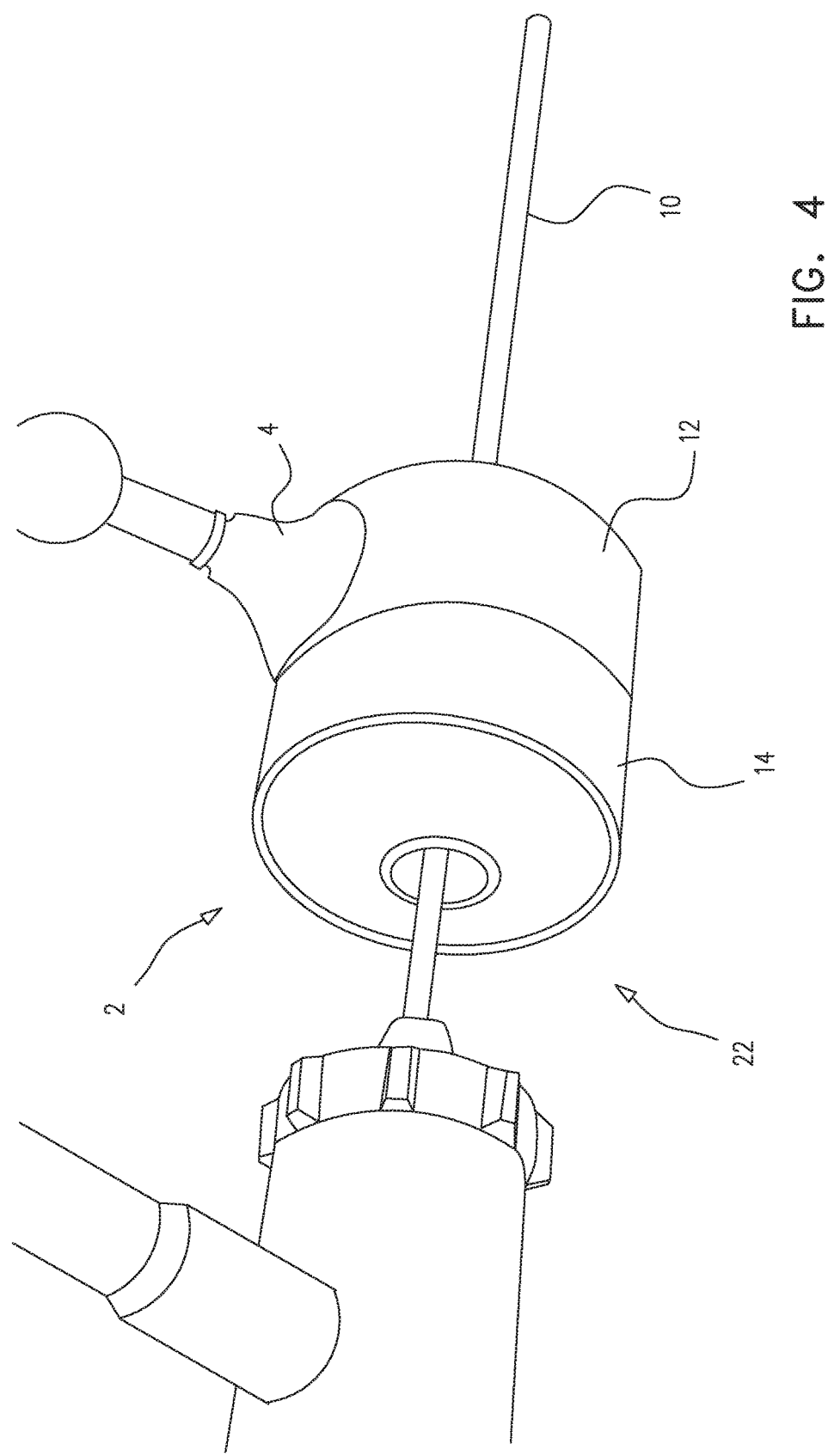
FIG. 4 is a schematic illustration of elements of apparatus for assisting a minimally-invasive surgical procedure, in accordance with some applications of the present invention.

Reference is made to FIG. 4, which is a schematic illustration of apparatus 2 for assisting a minimally-invasive surgical procedure, as provided in accordance with some applications of the present invention. As shown, apparatus 2 is mounted on shaft 10 of surgical tool 22. Apparatus 2 comprises first element 12 which is shown surrounding a first portion of shaft 10 of laparoscopic tool 22. First element 12 is coupled to laparoscopic tool support arm 4, such that laparoscopic tool 22 is coupled to laparoscopic tool support arm 4 via first element 12.

Additionally, apparatus 2 comprises second element 14 which is shown surrounding a second portion of shaft 10 of laparoscopic tool 22. Second element 14 is configured to change a position thereof with respect to first element 12 and as a result, control a disposition of laparoscopic tool 22 within the patient.

Figure 5:
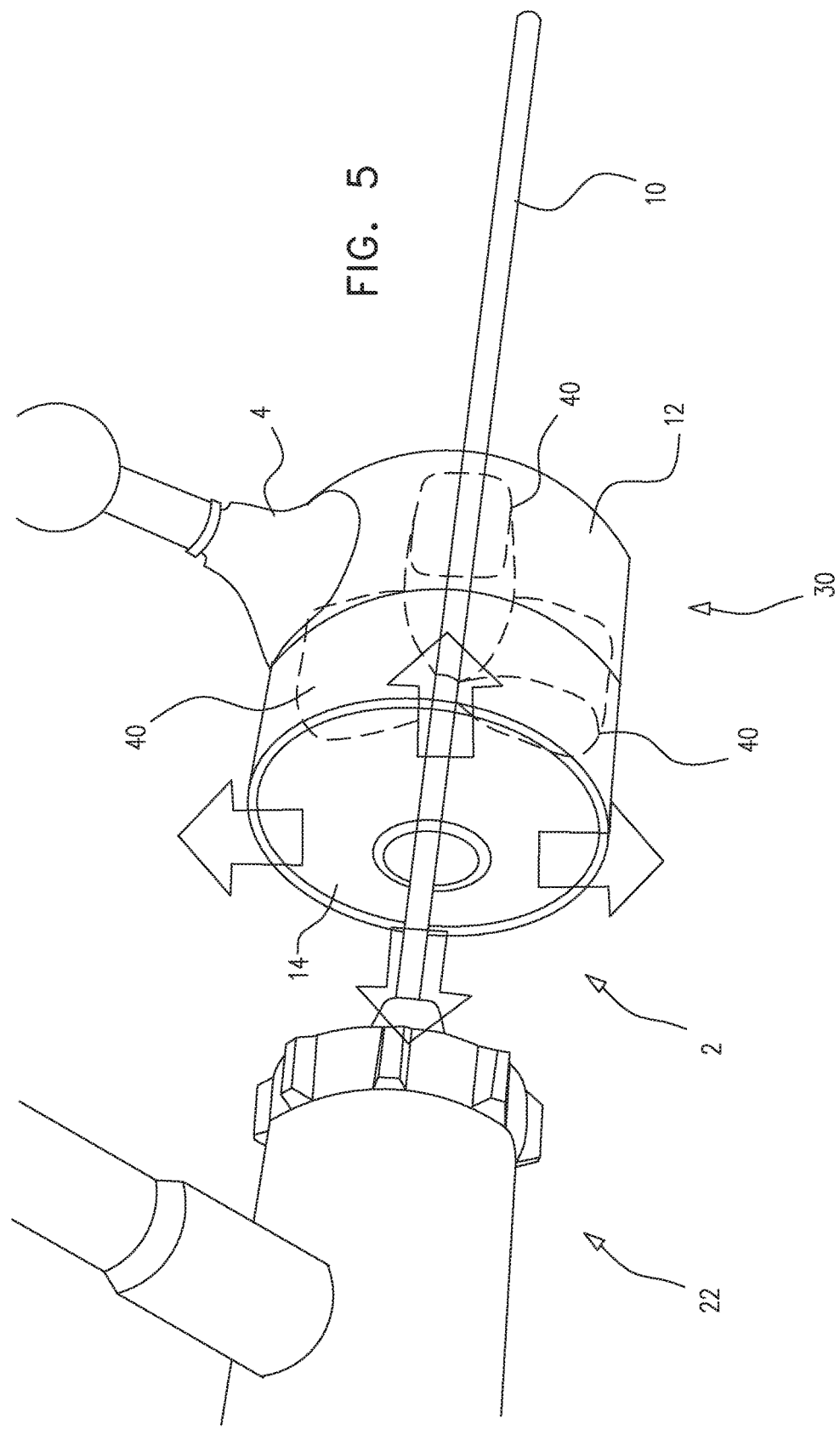
FIGS. 5 and 6 are schematic illustrations of an actuator unit of the apparatus for assisting a minimally-invasive surgical procedure, in accordance with some applications of the present invention.
Figure 6:
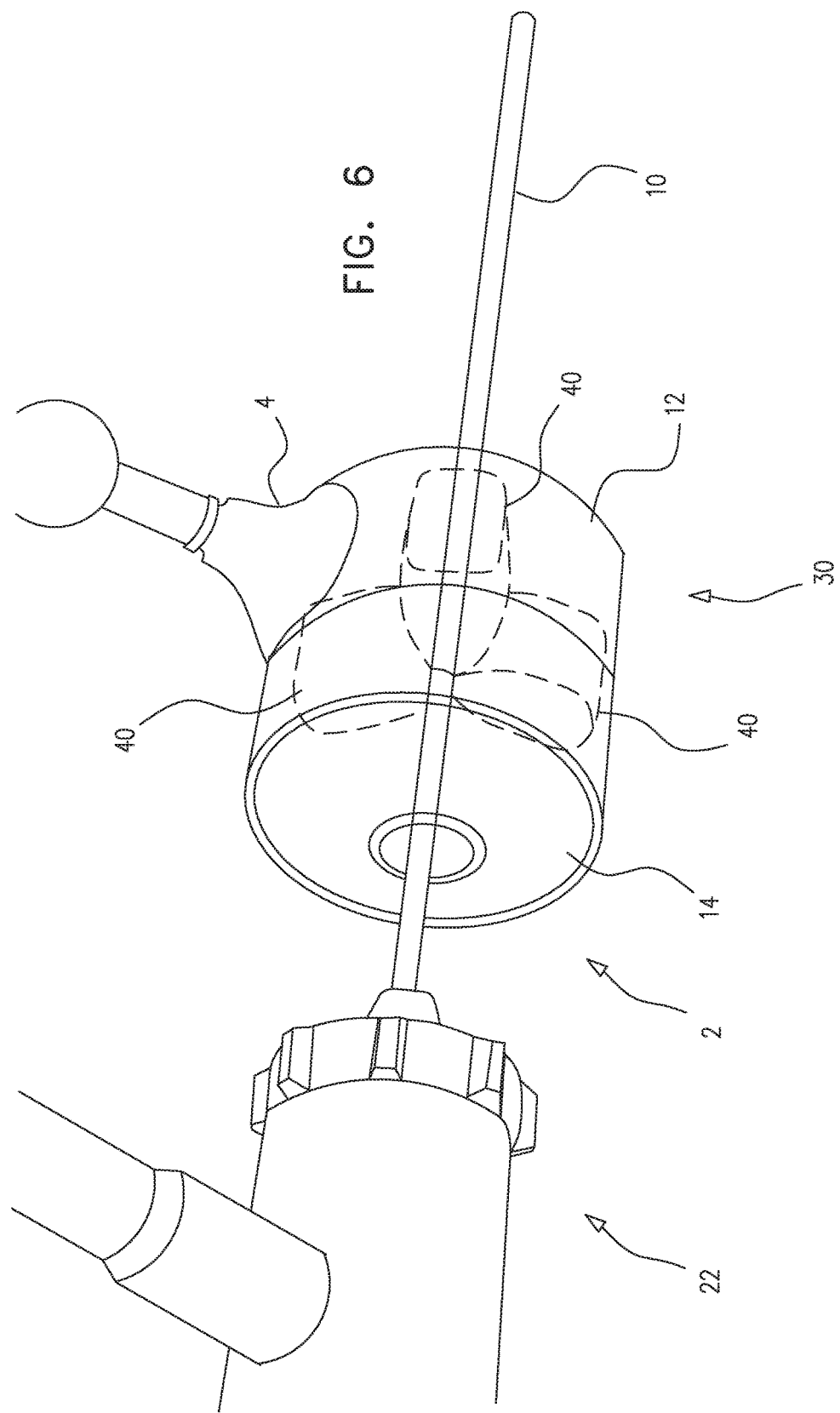
Figure 7:
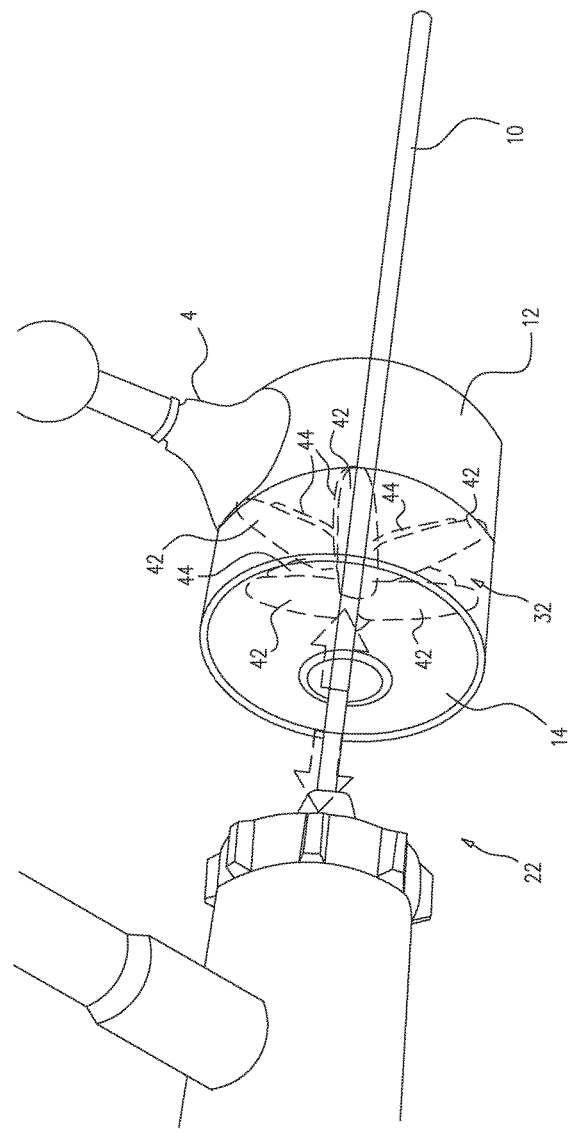
FIGS. 7 and 8 are schematic illustrations of an actuator unit of the apparatus for assisting a minimally-invasive surgical procedure, in accordance with some applications of the present invention.
Figure 8:
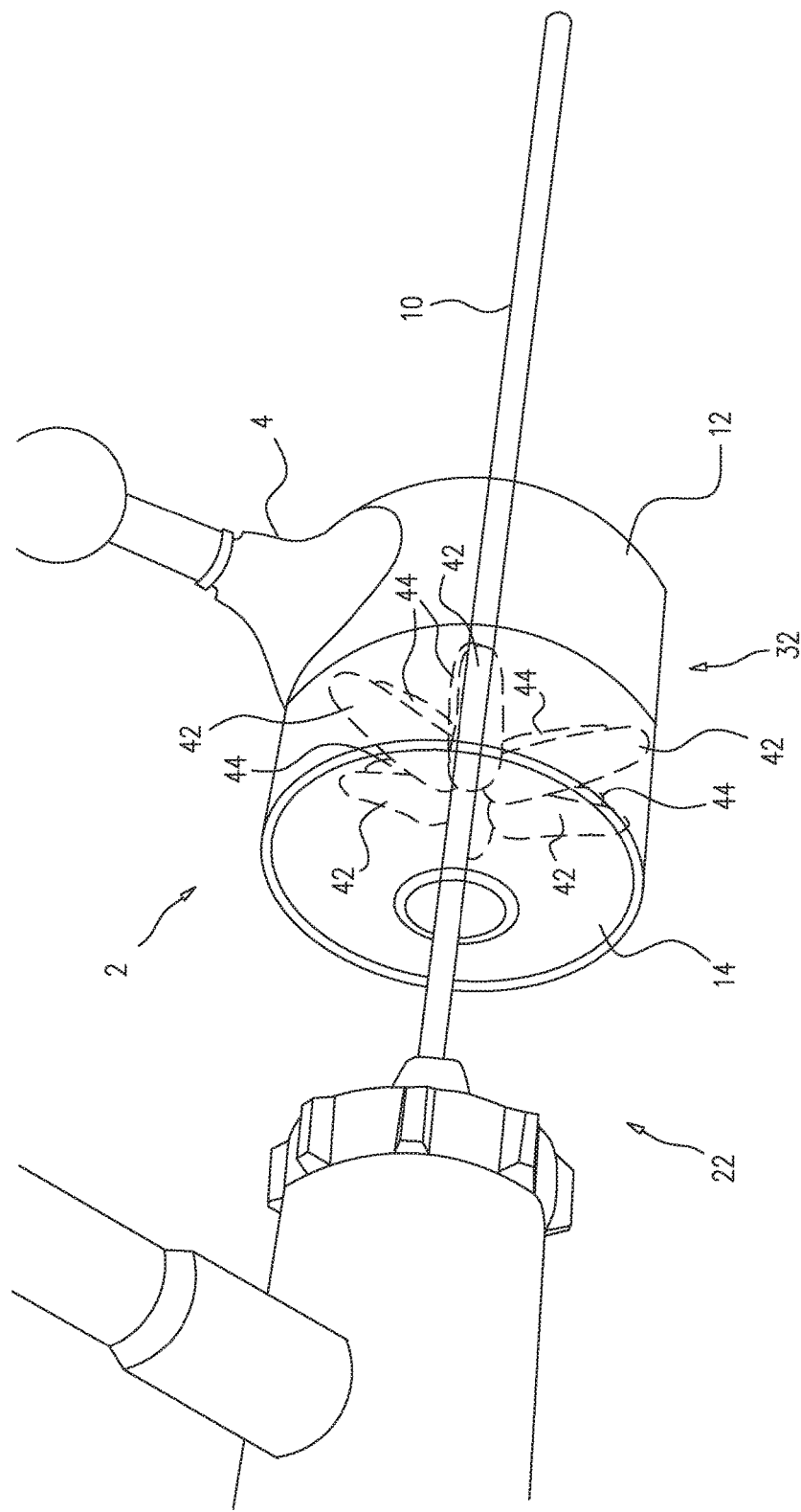

Reference is made to FIGS. 5 and 6, which are schematic illustrations of an actuator unit 30 of apparatus 2 for assisting a minimally-invasive surgical procedure, in accordance with some applications of the present invention. Element 12 (and/or element 14) typically comprises actuator unit 30. Actuator unit 30 controls a disposition of laparoscopic tool 22 within the patient by changing a relative position of element 14 with respect to element 12. For some applications, actuator unit 30 comprises one or more inflatable components 40, and inflation and deflation of components 40 lead to the re-positioning of element 14 with respect to element 12. As described hereinabove, re-positioning of element 14 with respect to element 12 controls movement of surgical tool 22 within the body of the patient.

Each inflatable component 40 is typically inflated by a distinct inflation lumen (e.g., running along or within the support arm 4), allowing selective inflation and deflation of each component 40. Inflation of one or more components 40 typically facilitates movement of tool 22 by applying pressure to shaft 10 (indirectly, as described hereinbelow, or directly), such that the relative position of element 14 is altered with respect to element 12. Inflation and deflation of components 40 typically allow left and right, and up and down motions as illustrated in FIGS. 5 and 6 (as well as combinations of up/down and right/left motions). FIG. 6 shows an example of inflation of two of components 40, and deflation of one of components 40, in order to elevate a proximal end of tool 22, and correspondingly lower a distal end (within the patient) of tool 22.

Additionally, for some applications, inflatable components 40 of second element 14 in effect comprise a locking and unlocking mechanism. Apparatus 2 is configured to lock onto tool shaft 10 by components 40 applying pressure to shaft 10 in an inflated state thereof. Deflation of components 40 typically unlocks element 14 and releases it from shaft 10. Alternatively or additionally, an additional inflatable locking component (not shown) disposed between first element 12 and second element 14 is inflated in response to a command by the operating surgeon, in order to prevent further motion of the first and second elements with respect to each other. For some applications, upon receiving a command to lock the first and second elements to each other, a processor of apparatus 2 drives the inflatable locking component to be inflated first, and then, once the relative positions of the first and second elements have thereby been secured, components 40 are inflated until they also secure second element 14 in place with respect to first element 12. (At that point, the inflatable locking component may be deflated.)

Typically, the locking and unlocking mechanism allows manual repositioning of the tool in the unlocked state of apparatus 2, and then subsequent locking of the tool in response to a command by the operating surgeon. Apparatus 2 is configured to lock onto surgical tool 22 anywhere along shaft 10. Apparatus 2 is typically configured for use with all existing laparoscopic surgery tools.

Reference is still made to FIG. 6. FIG. 6 shows components 40 acting directly on shaft 10 of tool 22. Alternatively, components 40, which are located in element 12, act on an extension portion of element 14 which extends from element 14, surrounds shaft 10, and is disposed within element 12 (configuration not shown). Actuation of components 40 within element 12 typically applies pressure to an outer surface of the extension portion of element 14, causing rotation of shaft 10 and the desired up/down and right/left motions of shaft 10.

Reference is made to FIGS. 7-10, which are schematic illustrations of an actuator unit 32 of apparatus 2, in accordance with some applications of the present invention. For some applications, actuator unit 32 is disposed in element 14 (and/or in element 12) and comprises one or more pairs of inflatable components 42 and 44. Typically (but not necessarily), components 42 are larger in size than components 44, as shown in FIGS. 9-10. Inflation and deflation of components 44 typically facilitates inchworm-like movement of shaft 10 in a proximal and distal direction (i.e., in/out motion that is towards and away from the internal organ of the patient).

As shown in the transition from FIG. 9 to FIG. 10, the inflation of components 44 acts as a lever for pushing components 42 in a proximal direction, resulting in movement of shaft 10 in a proximal direction, if pushing components 42 are in the inflated state and squeezing shaft 10. Thus, proximal (outward) motion of shaft 10 may be achieved by cyclic application of:

(a) inflation of component 42 while component 44 is in the deflated state (FIG. 9), followed by (b) inflation of component 44 while component 42 is in the inflated state (FIG. 10, producing the desired proximal motion), followed by (c) deflation of component 42 while component 44 is in the inflated state, followed by (d) deflation of component 44 while component 42 is in the deflated state.

Similarly, deflation of components 44 results in retraction of components 42 and pulling of shaft 10 distally, if pushing components 42 are in the inflated state and squeezing shaft 10. Thus, distal (into-the-patient) motion of shaft 10 may be achieved by cyclic application of:

(a) inflation of component 42 while component 44 is in the inflated state, followed by (b) deflation of component 44 while component 42 is in the inflated state (producing the desired distal motion of shaft 10), followed by (c) deflation of component 42 while component 44 is in the deflated state, followed by (d) inflation of component 44 while component 42 is in the deflated state.

The proximal and distal motions attained by the cyclic applications described immediately hereinabove produce stepwise motion in the desired direction (i.e., motion, then pause, then motion then pause). For some applications, if smoother motion is desired, a plurality of sets of components 44 and 42 are activated out of phase with each other (FIGS. 7 and 8), such that one set is producing the desired motion, while another set is inflating or deflating its components 44 and 42 in order to be ready to itself subsequently produce the desired motion.

Typically, apparatus 2 comprises both actuator unit 30 and 32. For some applications, first element 12 comprises actuator unit 30 for movement of element 14 for achieving up/down and right/left motions of shaft 10, while second element 14 comprises actuator unit 32 for in/out movement of shaft 10.

Linear Slide Pneumatic Motor

Reference is now made to FIGS. 11A-H, which show a mechanism for a linear slide implemented via a pneumatic stepper motor assembly 22 operating via small, discrete motions, driven by inflation and deflation of small-volume balloons.

For some applications, surgical control apparatus comprises first and second rails 140, and a pneumatic stepper motor assembly 22 which is configured to slide first and second rails 140 in a direction indicated by the arrows.

Generally, motor assembly 22 comprises first and second motor subassemblies 180/185 which comprise two sets of balloons, each set comprising first and second motor subassembly-locking balloons 160/165 and first and second motor subassembly-moving balloons 170/175 coupled to the first and second motor subassemblies, respectively. Locking balloons 160/165 are used to 'lock' first and second movable rail 140 respectively, to a moving part 130 of the motor subassembly, while moving balloons 170/175 are used to move first and second rails 140 a single motion step with respect to stationary base 100 of motor assembly 22.

More specifically, motor assembly 22 comprises a first motor subassembly 180 having moving part 130 and comprising a first-motor subassembly locking balloon 160, configured to lock first rail 140 to the first motor subassembly by inflation of balloon 160. First motor subassembly 180 additionally comprises a first-motor subassembly moving balloon 170 configured to move first rail 140 (along with second rail 140) by a mechanism selected from the group consisting of: a) inflation of moving balloon 170, when the locking balloon 160 is inflated, and b) deflation of the moving balloon 170, when balloon 160 is inflated.

Motor assembly 22 further comprises a second motor subassembly 185 having moving part 130, and comprising a second-motor subassembly locking balloon 165, configured to lock second rail 140 to the second motor subassembly by inflation of balloon 165. Second motor subassembly 185 additionally comprises a second-motor subassembly moving balloon 175 configured to move second rail 140 (along with first rail 140) by a mechanism selected from the group consisting of: a) inflation of moving balloon 175, when the locking balloon 165 is inflated, and b) deflation of the moving balloon 175, when balloon 165 is inflated.

The locking action is performed by inflating locking balloon 160/165 to fill a small gap between rail 140 and part 130, thus imparting a normal force on rail 140 and locking it to moving part 130. The normal force is typically translated into high friction that 'locks' rail 140 and moving part 130 together during motion. The friction can be increased, for example, by adding a high friction material between balloon 160 and rail 140, and/or by coating an external surface of balloon 160 with a material having high friction properties. Once balloon 160 is inflated and rail 140 is 'locked' to moving part 130, inflation of balloon 170 moves part 130 and rail 140 together with balloon 160 a desired motion step. For some applications, stationary base portion 100 comprises upper and lower anchoring elements 120 that anchor balloon 170/175 and/or a spring 150.

Additionally or alternatively, motor assembly 22 includes stationary rollers 110 that allow low-friction movement of rails 140.

FIG. 11A shows balloons 160 and 170 in a deflated state thereof. A single motion step comprises inflation of balloon 160 (as shown in FIG. 11B) followed by inflation of balloon 170 which advances rails 140 in the up direction of the figures (as shown in FIG. 11C).

The size of the motion step (i.e., the degree of advancement of rail 140) is typically determined by the distance that inflated balloon 170 is advanced along the direction of motion, and is typically 0.1-1.0 mm.

As described hereinabove, for some applications, motor assembly 22 and base portion 100 additionally include one or more loading springs 150. Spring 150 typically opposes the movement of moving part 130 induced by inflation of balloon 170/175. Spring 150 typically facilitates continuous control over the motion step size by changing the inflation pressure of balloon 170/175 and the spring constant of spring 150, such that the force applied by balloon 170/175 corresponds to a certain displacement of spring 150. For example, a surface area of balloon 170 may be 1 cm$^2$, a force constant of spring 150 may be 10 kgF/mm, and a variable step size between 0.25 mm and 1 mm is chosen by varying an inflation pressure of balloon 170 between 2.5 and 10 Atmospheres, respectively.

Alternatively, for some applications, spring 150 has a relatively small spring constant, and the motion step is determined by the distance between anchoring elements 120. In such applications, when balloon 170/175 is deflated, spring 150 pushes moving part 130 with a force equal to its preloading force, until part 130 is stopped by lower anchoring element 120. When balloon 170/175 is inflated, it pushes moving part 130 with a force larger than the force imparted by spring 150, until part 130 is stopped by upper anchoring element 120. The difference in force between the inflated balloon force and the loaded spring force creates a 'force hysteresis'—a range of force strength where the system will not move in response to external forces.

For example, the forces exerted by the spring and balloon might be 2 kgF for the spring, and 4 kgF for inflated balloon 170/175. When balloon 170/175 is deflated, an external force smaller than 2 kgF will be unable to displace the mechanism, due to the force exerted by the spring; the same is true when the balloon is inflated, since the difference between the balloon force and spring force is also 2 kgF.

Changing the order of balloon inflation and deflation allows reversing of the motion direction. A sequence of operations in which:

a) moving balloon 170 is inflated and 'loads' spring 150 (FIG. 11D);

b) locking balloon 160 is inflated and 'locks' rail 140 (FIG. 11C); and c) moving balloon 170 is deflated, allowing spring 150 to 'unload' (FIG. 11B), will move rail 140 a step in the 'reverse' direction.

Generally, continuous multi-step motion is achieved by using two such symmetrical sets of balloons, 160/165 and 170/175, and springs 150. While first moving balloon 170 moves first rail 140 a single step, second locking balloon 165 is deflated, and second moving balloon 175 is either deflated or inflated to prepare for the next step. After completion of the motion step, the next step is taken by inflating second locking balloon 165 and deflating first locking balloon 160. Generally, at least one rail 140 is 'locked' to assembly 22 by having at least one of locking balloons 160 and 165 inflated. This sequence can repeat as many times as necessary to create a large motion range of the mechanism. Control over motion step size is continuous and adjustable, since the step size is continuously variable (as described above), and motion velocity is determined by balloon inflation and deflation times. For example, in some applications the step size might be 0.5 mm, with 10 ms switching time for a single step motion, and maximum velocity of 50 mm/sec.

Figure 11E:
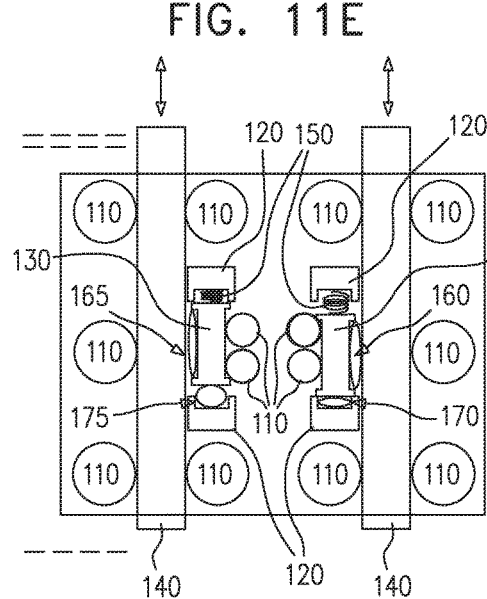
Figure 11F:
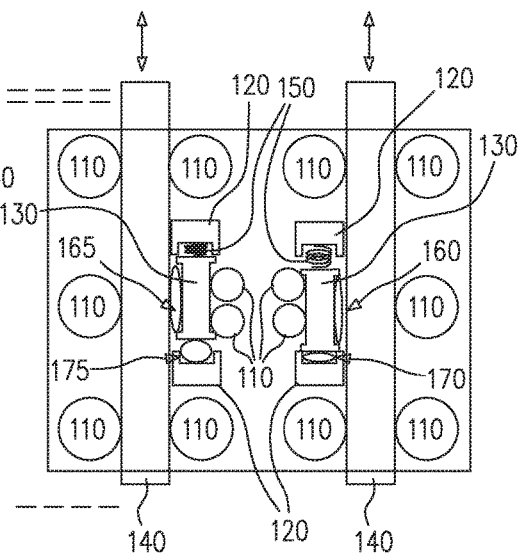
Figure 11G:
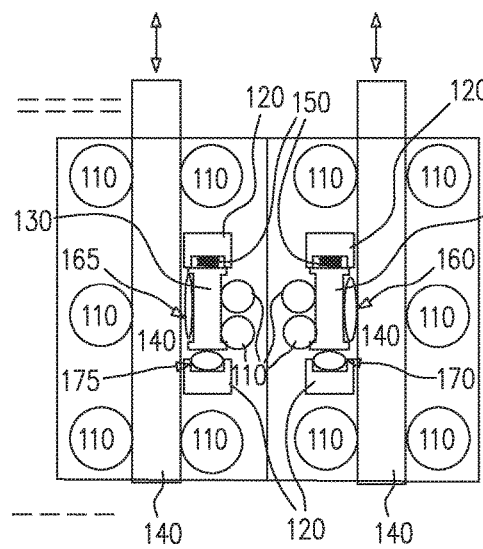
Figure 11H:
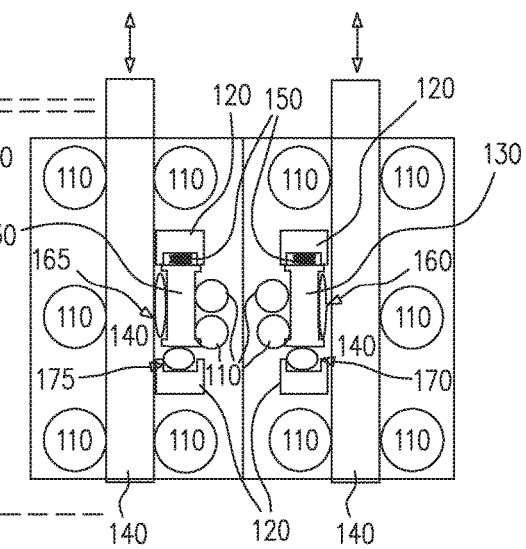

FIG. 11E shows balloon 160 inflated thereby locking moving part 130 to rail 140, and moving balloon 175 inflated and loading spring 120. A motion step comprises inflating locking balloon 165 and deflating locking balloon 160 (FIG. 11F) and moving balloon 175 advancing rail 140 in an up direction (FIG. 11G).

A cross-section of motor assembly 22 (shown by way of example in FIG. 11B), shows a slide 142 having two parallel rails 140 passing through two sets of rollers 110. Motor assembly 22 typically has dual integrated single-step sub-mechanisms; each single-step subunit moves one of parallel rails 140 (and, correspondingly, the other rail 140), and together the pneumatic stepper motor assembly provides generally full and continuous control of the motion. It is additionally noted that deflation of both locking balloons 160 and 165 allows free motion of rails 140. This 'quick release' mechanism is useful for manual adjustment of the position of slide 142.

Figure 12A:
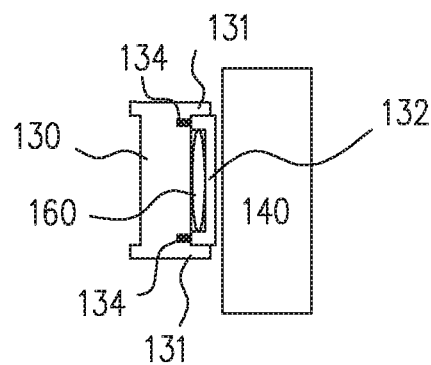
FIGS. 12A-B are schematic illustrations of a locking mechanism, in accordance with some applications of the present invention.
Figure 12B:
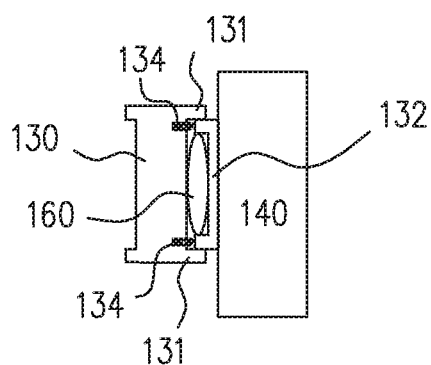

Reference is now made to FIGS. 12A-B which are schematic illustrations of a locking mechanism comprising a locking element 132, for use with a motor assembly as described hereinabove with reference to FIGS. 11A-H, in accordance with some applications of the present invention. In some applications of the present invention, locking balloon 160/165 is inflated and pushes locking element 132 against rail 140 as shown in FIG. 12B. Locking element 132 typically includes high friction material to inhibit slippage with respect to rail 140; thus, it acts like a brake pad, 'locking' rail 140 to moving part 130 via a strong frictional force. Locking element 132 is typically but not necessarily fixed to moving part 130 via return springs 134, which are restricted by moving-part 130 to movement only in the horizontal direction (as shown in the figure). Motion of locking element 132 is restricted by restricting walls 131 of moving element 130. Return springs 134 elongate when locking balloon 160 is inflated, the inflation pushing locking element 132 against rail 140.

Return springs 134 contract when locking balloon 160 is deflated, thus pulling locking element 132 back toward moving part 130, as shown in FIG. 12A. The interposition of locking element 132, along with the restriction of movement to the horizontal direction, prevent shear forces from distorting and/or otherwise compromising the integrity of locking balloons 160/165, and also provide that moving part 130 and rail 140 move a generally equal distance upon inflation or deflation of moving balloons 170/175 (shown in FIGS. 11A-H). (Since the locking balloon material is flexible in order to allow expansion, it also allows distortion by which the inflated balloon shape becomes like a parallelogram. If locking balloon 160/165 were to contact rail 140 directly, only the side of the balloon adjacent to moving part 130 would move with part 130; the side of the balloon adjacent to rail 140 would stay in place or move less than the displacement of moving part 130.) In addition, it is noted that use of locking element 132 allows locking balloons 160/165 to be very thin-walled (e.g., 0.05-0.15 mm, e.g., 0.1), because balloons 160/165 are constrained from excess expansion and bursting by locking element 132.

Reference is now made to FIGS. 13A-F, which is a schematic illustration of an additional mechanism for a linear slide, in accordance with some applications of the present invention. Techniques and apparatus described hereinabove with respect to FIGS. 11A-H are generally used in the mechanism of FIGS. 13A-F, except where indicated to the contrary. In some applications, the mechanism of FIGS. 13A-F is combined with the locking element functionality described herein with respect to FIGS. 12A-B.

FIGS. 13A-F show a pneumatic stepper motor assembly 24 in which moving balloon 470 is disposed at the bottom end of right moving part 130, while moving balloon 475 is disposed at the top end of left moving part 130. Movement of rails 140 in the down direction of the figures is effected via the following sequence of operations:

a) Locking balloon 160 is deflated while locking balloon 165 remains inflated (FIG. 13A).

b) Moving balloon 475 is inflated, thus moving rails 140 and loading left spring 450; at the same time, moving balloon 470 is inflated (e.g., via a common inflation tube), thus loading right spring 450 (FIG. 13B).

c) Locking balloon 160 is inflated, and locking balloon 165 is subsequently deflated (FIGS. 13C-D).

d) Moving balloon 470 is deflated, thus moving rails 140 and unloading right spring 450; at the same time, moving balloon 475 is deflated, thus unloading left spring 450 (FIG. 13E).

e) Locking balloon 165 is inflated (FIG. 13F). Following the inflation of locking balloon 165, the sequence of operations repeats itself.

It is noted that, in the mechanism shown in FIGS. 13A-F, moving balloons 470 and 475 are simultaneously inflated or deflated; thus, they can use a common pneumatic valve control.

X/Y Pneumatic Motor

Combining the principles of a pneumatic motor with a linear slide, as described hereinabove with reference to FIGS. 11A-H and 13A-F, provides means to build a compact X/Y motion stage. The linear slide size generally determines the motion range of the system. FIGS. 11A-H show the mechanism for a linear slide in X or Y directions, since two sets of single step mechanisms are provided for generally continuous motion. Combination of the X and Y direction slides provides XY motion.

Combining two slides in an orthogonal configuration gives full XY motion, as illustrated in FIGS. 14A-B. The 'ball' (labeled "RZ") in FIGS. 14A-B is a combined pneumatic push/pull (Z) and rotation (R) control for a surgical tool shaft manipulation. The principle of operation of these is explained hereinbelow, in the sections labeled Rotation Pneumatic Motor and Shaft Push/Pull Pneumatic Motor.

It is noted that, with respect to all of the examples described herein and shown in the figures, balloon-based operation typically forms the basis of the function of the pneumatic motors described.

It is additionally noted that, the principles described herein with respect to operation of the pneumatic mechanisms are not limited to a linear slide and/or shaft. Mechanisms described herein can be implemented for movement of a curved slide instead of a linear slide, where the curved slide moves in a circular arc around a center position outside the slide. For example, the curved slide can be designed such that the center of the arc corresponds to a trocar position where the surgical tool enters the patient's body in laparoscopic surgery.

Rotation Pneumatic Motor

A pneumatic motor for rotation of a shaft is typically designed by combining locking of the shaft and discrete shaft rotation. For such applications, the principles outlined herein for linear motion can be used to provide stepwise rotational motion to a shaft.

Reference is made to FIGS. 15A-B, which are schematic illustrations of two cross sections of a pneumatic motor mechanism 200, comprising a round shaft 240 passing through a round hole in mechanism 200. A locking balloon 260 is used to 'lock' shaft 240 to a moving part 230. Inflation of a moving balloon 270 pushes an extended lever portion of part 230, resulting in a clockwise rotation step for shaft 240. A counterclockwise rotation sequence includes first inflation of moving balloon 270, while locking balloon 260 is deflated, followed by inflation of locking balloon 260 and deflation of moving balloon 270. Motor mechanism 200 typically comprises two similar sets of balloons and springs which provide generally continuous control over rotation of shaft 240, and unlimited rotation of shaft 240. Typically, motor mechanism 200 additionally comprises anchoring elements 220 that anchor balloon 270 and spring 250. Rotation step size can be varied by balancing the spring constant of spring 250 and inflation pressure of moving balloon 270, or by changing the extension length of the lever portion of moving part 230. For a typical displacement step of 0.5 mm, shaft 240 diameter of 5 mm, and moving-part 230 lever length of 1 cm from the center of shaft 240, a rotation step size of about 3° is achieved. At 120 steps per second the maximal rotation rate is 1 rotation/sec.

Shaft Push/Pull Pneumatic Motor

Reference is made to FIGS. 16A-F, which are schematic illustrations of a tool shaft 940, locked and moving longitudinally along a shaft axis, in accordance with some applications of the present invention. FIGS. 16A-F show a push/pull pneumatic motor mechanism 900 for locking of tool shaft 940 and moving it along the shaft axis. Techniques and apparatus described hereinabove with respect to FIGS. 11A-H and 13A-F are generally used in the mechanism of FIGS. 16A-F, except where indicated to the contrary. In some applications, the mechanism of FIGS. 16A-F is combined with the locking element functionality described herein with respect to FIGS. 12A-B.

FIGS. 16A-F show pneumatic stepper motor mechanism 900 comprising a set of locking balloons 960/965, which 'lock' shaft 940 to moving parts 930/935 respectively, and a set of moving balloons 970/975 configured to move shaft 940 along the shaft axis.

Typically, motor mechanism 900 additionally comprises springs 950/955 and anchoring elements 920. Anchoring elements 920 anchor balloons 970/975 and springs 950/955. It is noted that springs 950/955 and anchoring elements 920 generally correspond to springs 150 and anchoring elements 120 described hereinabove.

Figure 16A:
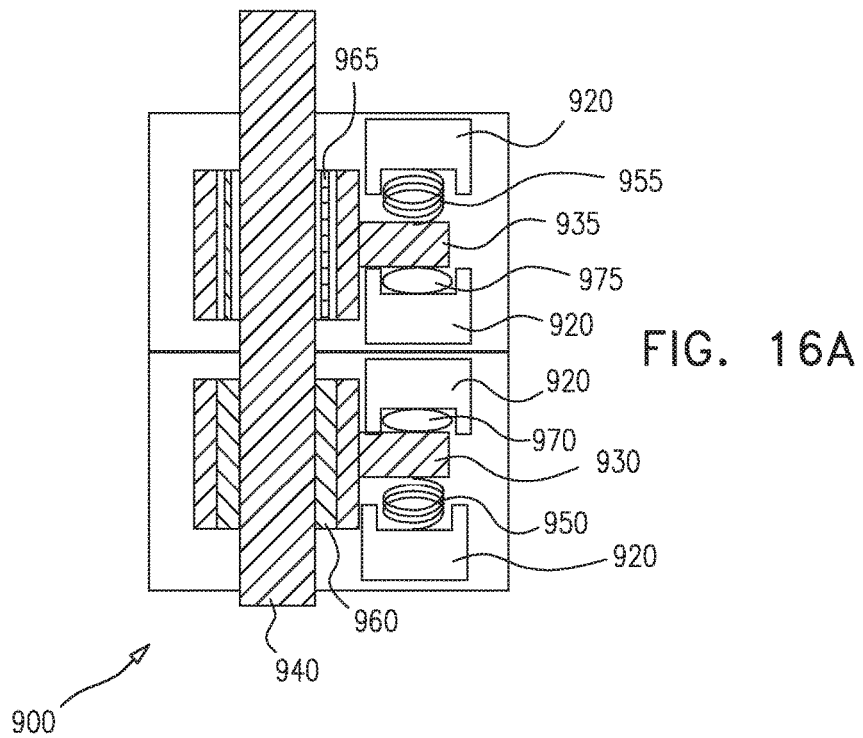
FIGS. 16A-F are schematic illustrations of a tool shaft, lockable and movable along a shaft axis, in accordance with some applications of the present invention.

Movement of shaft 940 in the down direction as shown in the figures is effected via the following sequence of operations:

FIG. 16A: Locking balloon 960 is inflated to 'lock' shaft 940 to moving part 930 of mechanism 900 (locking balloon 960 is shown as a 'doughnut' balloon encircling shaft 940), while locking balloon 965 remains deflated.

Figure 16B:
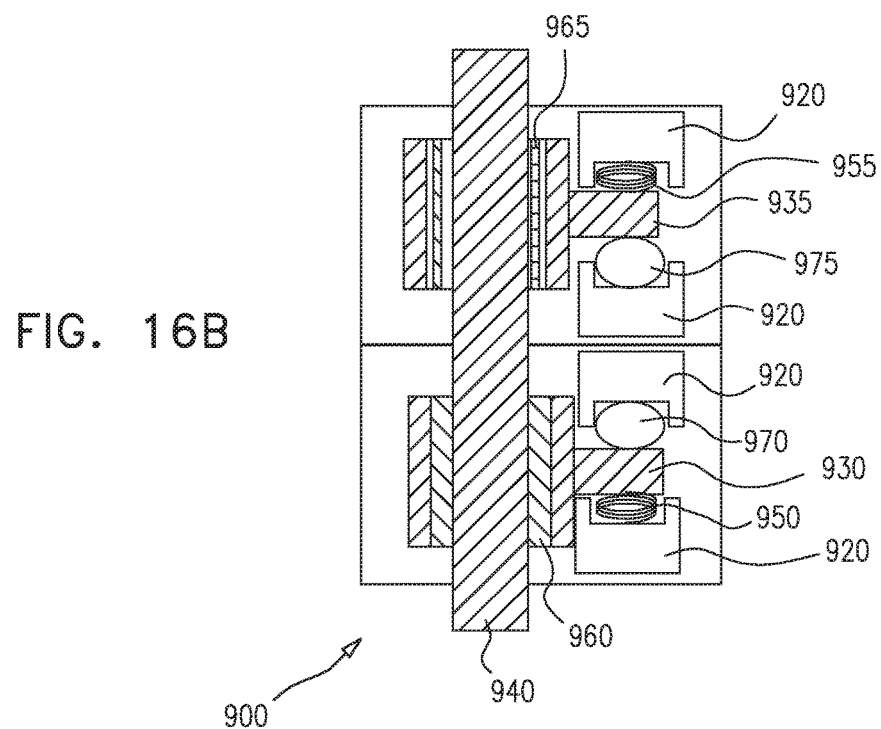

FIG. 16B: Moving balloon 970 is inflated, thus moving shaft 940 down in the figure and loading spring 950; at the same time, moving balloon 975 is inflated (e.g., via a common inflation tube), thus loading spring 955. (It is noted that the inflation of moving balloon 975 in this step does not result in movement of moving shaft 940, because locking balloon 965 is not inflated.)

Figure 16C:
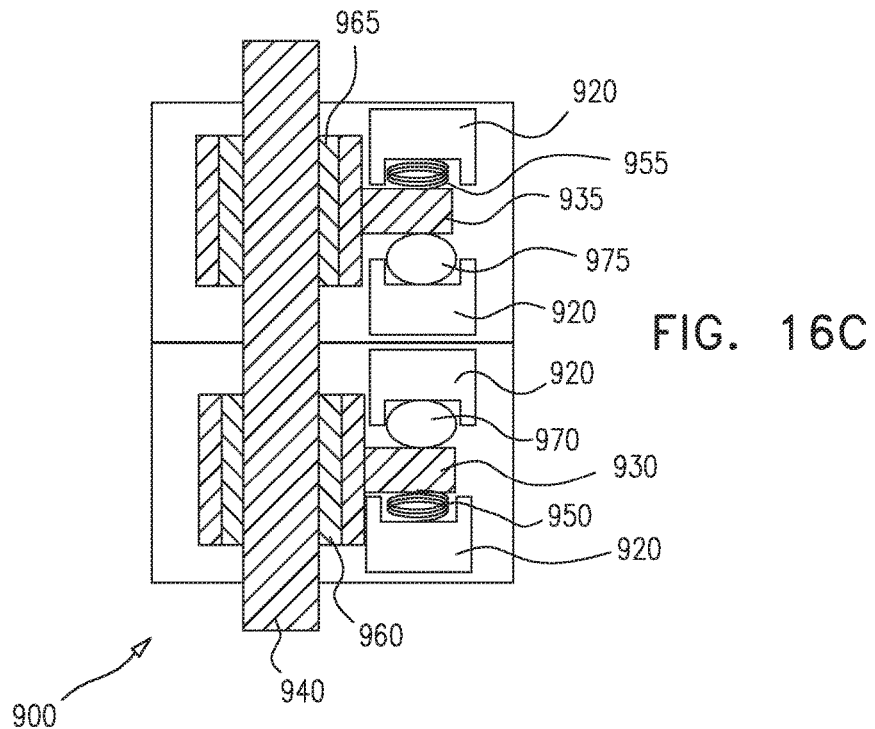

FIG. 16C: Locking balloon 965 is inflated.

Figure 16D:
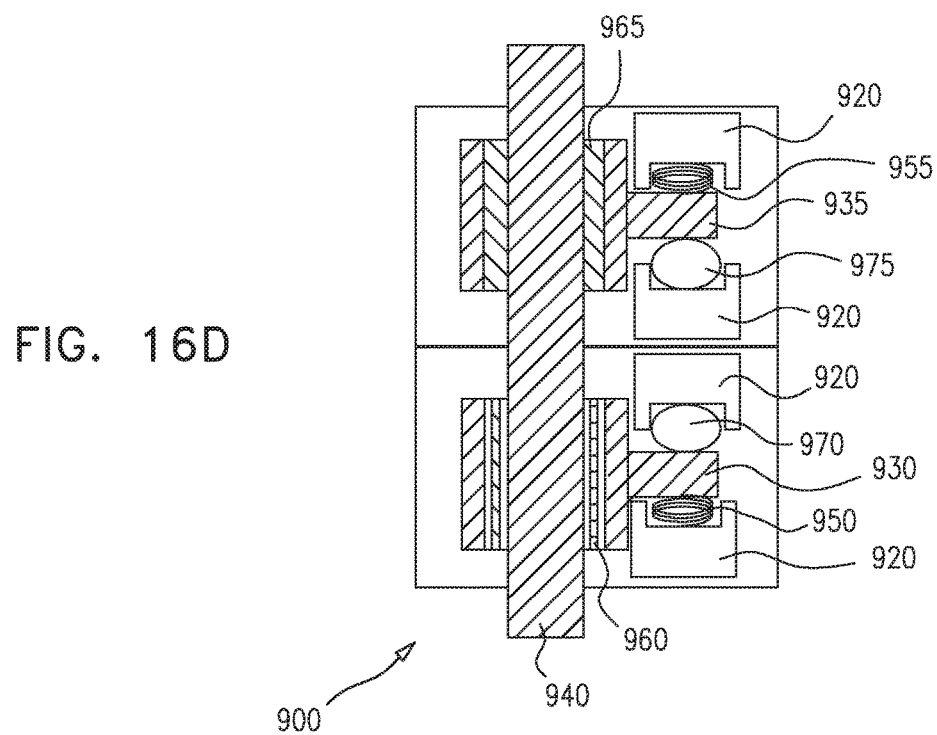

FIG. 16D: Locking balloon 960 is deflated.

Figure 16E:
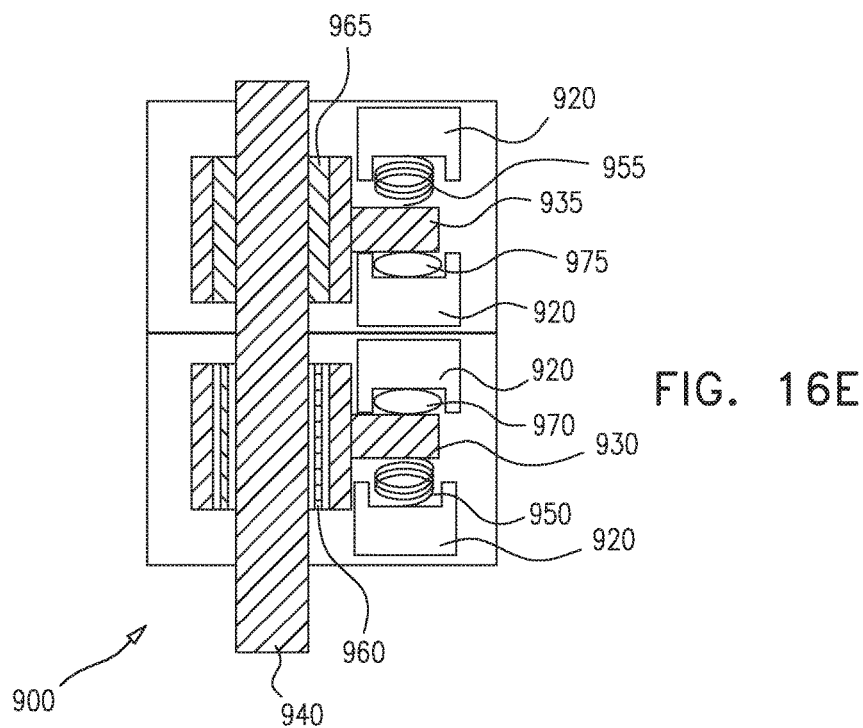

FIG. 16E: Moving balloon 975 is deflated, thus moving shaft 940 in the down direction in the figure and unloading spring 955; at the same time, moving balloon 970 is deflated, thus unloading spring 950.

Figure 16F:
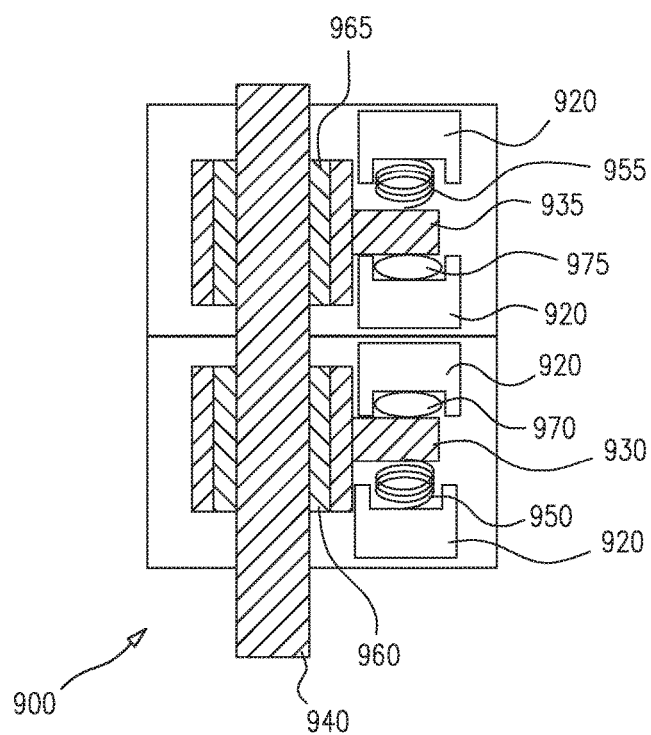

FIG. 16F Locking balloon 960 is inflated. Following the inflation of locking balloon 960, the sequence of operations repeats itself.

It is noted that, in the mechanism shown in FIGS. 16A-F, moving balloons 470 and 475 are simultaneously inflated or deflated; thus, they can use a common pneumatic valve control.

Figure 24:
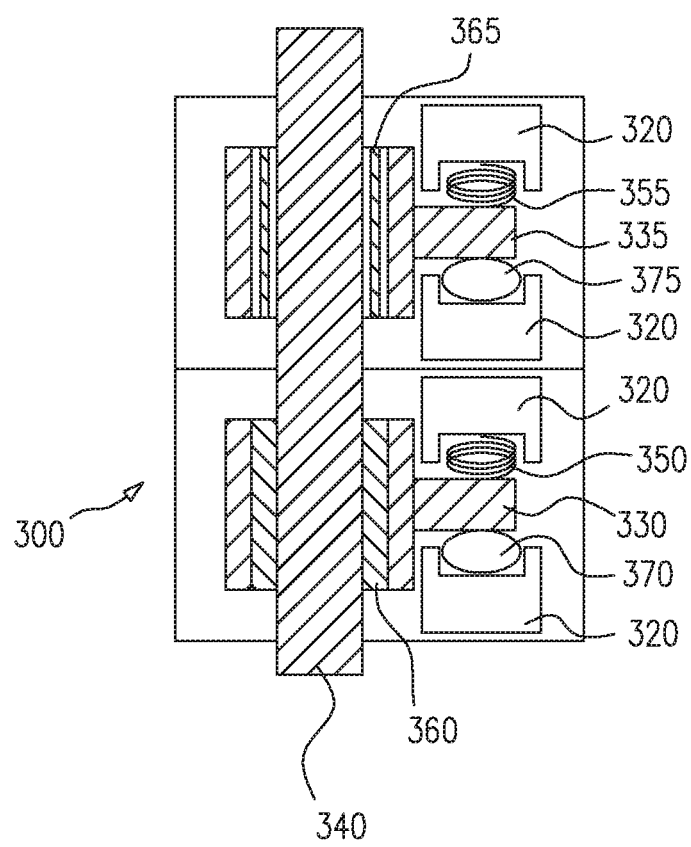
FIG. 24 is a schematic illustration of a tool shaft, locked and moving along a shaft axis, in accordance with some applications of the present invention.

An additional Shaft Push/Pull mechanism is shown in FIG. 24 which is a schematic illustration of a tool shaft, locked and moving along a shaft axis, in accordance with some applications of the present invention. FIG. 24 shows a push/pull (in/out) pneumatic motor mechanism 300 for locking of a tool shaft 340 and moving it along the shaft axis. (Only one phase of the overall cycle is shown; however, the same concepts described hereinabove with reference to FIGS. 11A-H may be applied with reference to FIG. 24.)

Shaft 340 (shown in cross section) is 'locked' to moving part 330 of mechanism 300 by inflating locking balloon 360 (shown as a 'doughnut' balloon encircling shaft 340). Inflation of a moving balloon 370 will push a lever section of part 330 and move shaft 340 a step in the 'up' direction of the drawing. The motion in the 'down' direction is by reversing the balloon inflation and deflation sequence, and the step size is variable in the same manner as described for X/Y motion. A second, corresponding mechanism, including locking balloon 365 and moving balloon 375, and a moving part 335, is used for generally continuous and unlimited push/pull motion of shaft 340. Typically, motor mechanism 300 additionally comprises springs 350/355 and anchoring elements 320 that anchor balloons 370/375 and springs 350/355. It is noted that springs 350/355 and anchoring elements 320 are generally the same as springs 150 and anchoring elements 120 described hereinabove.

Figure 17:
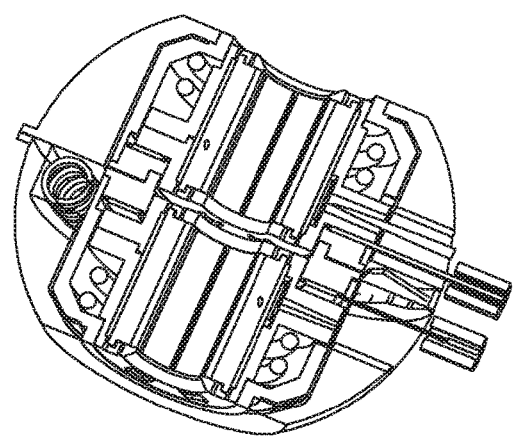
FIG. 17 is a schematic illustration of a design of two subunits integrated into a single push/pull and rotation pneumatic stepper motor mechanism, in accordance with some applications of the present invention.

The cross section in FIG. 17 shows the design of two subunits integrated into a single push/pull and rotation pneumatic stepper motor mechanism, in which mechanism 300, shown in FIG. 16, has been integrated with mechanism 200, shown in FIG. 15A-B. In this design, shaft 240 and shaft 340 are the same shaft, and locking balloons 260 and 360 are the same balloon. The same combined mechanism is shown in FIGS. 14A-B as part of a XYZ-Rotation mechanism, providing four degrees of freedom.

It is noted that, the concept of a return spring, and an element that prevents deformation of the locking balloon due to shear forces (as in FIGS. 12A-B), can be likewise incorporated into the push-pull and/or rotation mechanisms shown in FIGS. 15A-B, 16, and 17.

Pneumatic Tool Operation

The principle of pneumatic motion of a shaft can also be used for pneumatic remote control of Minimally Invasive Surgery (MIS) tool operation—closing and opening a tool handle with a controlled motion range and force.

Figure 18:
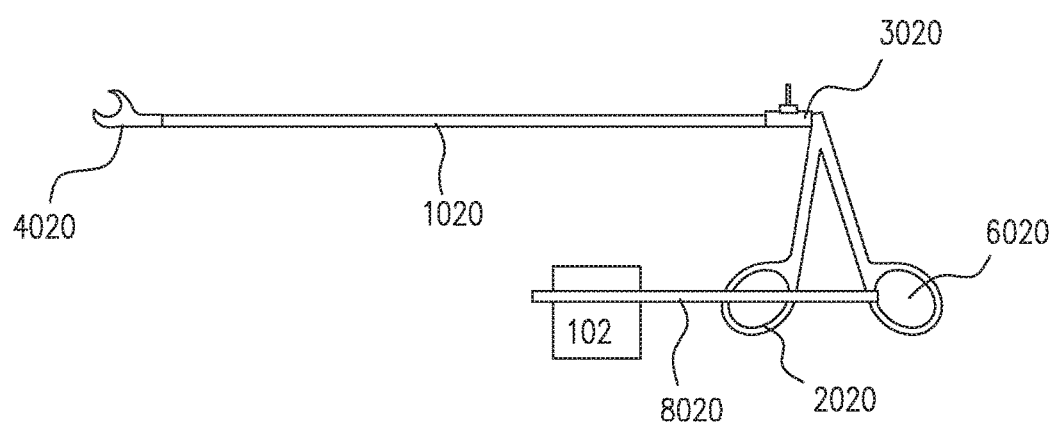
FIG. 18 is a schematic illustration of a laparoscopic tool handle with an insert connected to a pushrod, in accordance with some applications of the present invention.

For example, as shown in FIG. 18, one implementation is to connect a pushrod to the tool handle and use a push/pull pneumatic motor (e.g., as described hereinabove) to move the pushrod for closing and opening the tool (scissors, grabber, etc.). The motion can be discrete—using a pneumatic 'stepper' motor configuration, or generally continuous—using a proportional pressure regulator valve to move a bellows type balloon mechanism.

Measuring the force exerted on the pushrod by the movement and locking balloons allows for controlling the force exerted by the tool and for safety mechanisms to stop the motion in case of increased resistance. Thus, the moving pushrod can be made to 'slide' if the force desired to close the tool handle is more than the locking balloon force exerted on the pushrod. In a similar manner, the pressure in the moving balloon can be set to a level that limits the force exerted by the locked pushrod, and excessive resistance will typically stop the motion of the mechanism.

FIG. 18 shows a laparoscopic tool handle 2020 with a finger insert 6020 connected to a pushrod 8020. The pneumatic push/pull mechanism 102 can be generally similar to mechanism 300, and can be part of a more extensive robotic control unit that allows full control of both position and operation of the surgery tool (e.g., as shown hereinbelow with reference to FIG. 23). FIG. 18 also shows a tool shaft 1020, tool handle 3020, and surgical tool 4020, which can comprise, for example, a grabber or scissors.

Examples of Pneumatic Motor Assemblies Design

The principles described hereinabove, for example, with reference to FIGS. 11A-H and 12A-B, can be applied to the design of a balloon motor linear motion stage that can be mass manufactured and assembled in accordance with applications of the present invention. One such design is shown in FIGS. 19A-B.

Figure 19A:
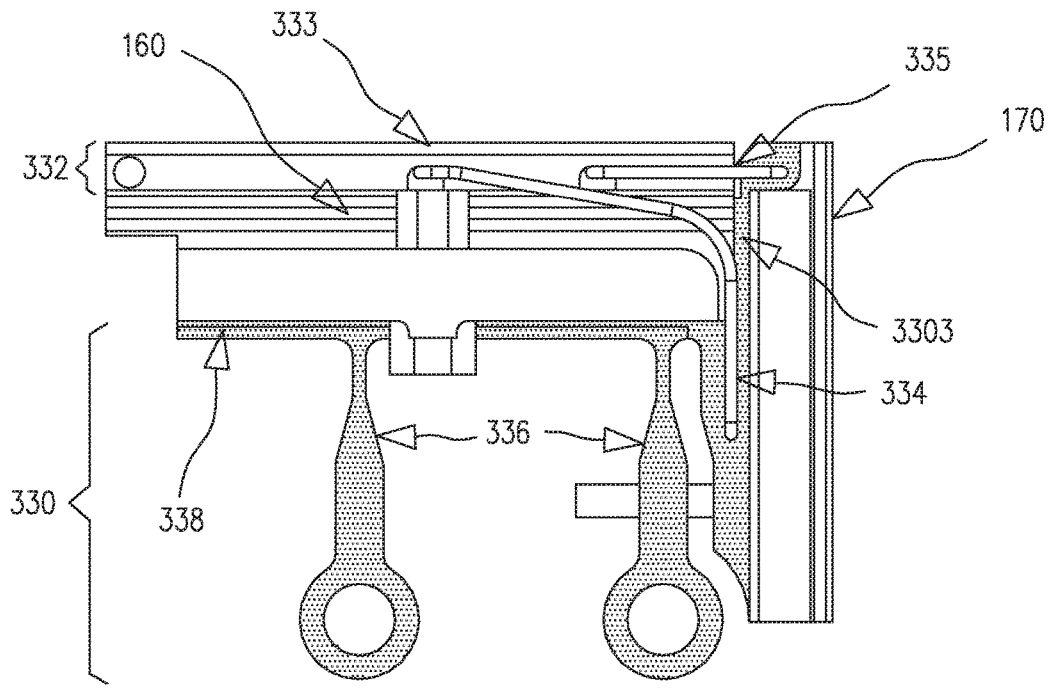
FIGS. 19A-B are schematic illustrations of a pneumatic motor assembly, in accordance with some applications of the present invention.
Figure 19B:
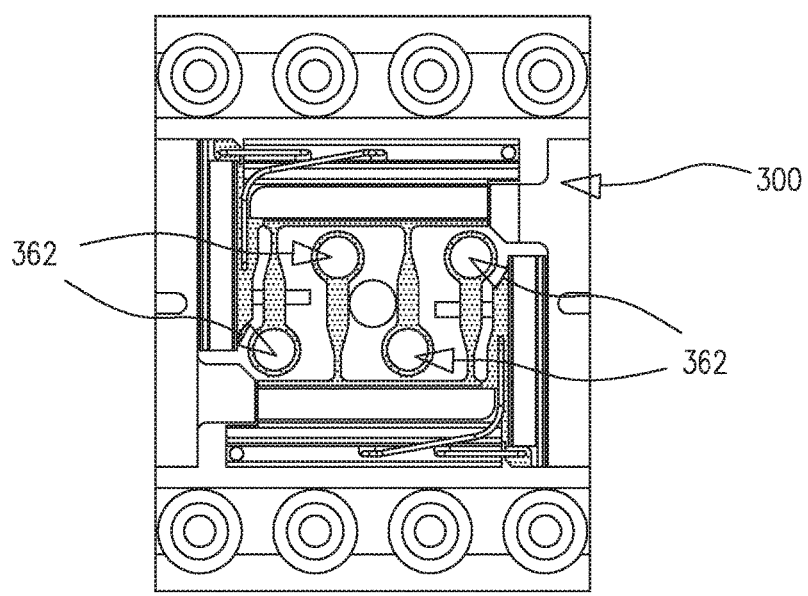

FIG. 19A shows moving balloon 170 and locking balloon 160, using similar principles of operation as those shown in FIGS. 11A-H. Rollers 110 and moving part 130 are replaced in this design by a single part 3303. Part 3303 comprises two pivots 336, which allow part 3303 to move like a four-bar mechanism. The upper part 338 of part 3303, which holds locking balloon 160, moves in the left and right direction in the figure, with generally negligible up and down motion. Pins 362, extending upward from the stationary base 3003 (FIG. 19B), fit through the round holes of pivots 336 and enable part 3303 to pivot with respect to pins 362 (e.g., counter-clockwise in FIGS. 19A-B). A locking element 332, functioning as a brake pad, has a high friction coating 333, and is connected by a bent spring 334 and straight link 335 to part 3303. The link 335 serves to generally restrict the motion of locking element 332 to motion which is in the up and down direction in the figure during inflation and deflation of balloon 160, and to prevent shear forces from affecting locking balloon 160. The use of link 335 to restrict the motion of locking element 332 typically reduces friction relative to the design shown in FIGS. 12A-B, where the motion is restricted by walls 131 of moving element 130. Spring 334, which generally plays the role of springs 134 in FIGS. 12A-B, returns locking element 332 to its original position upon deflation of locking balloon 160. High friction coating 333 comprises, for example, a rubber or silicone element. In some applications, coating 333 is also textured.

Figure 20A:
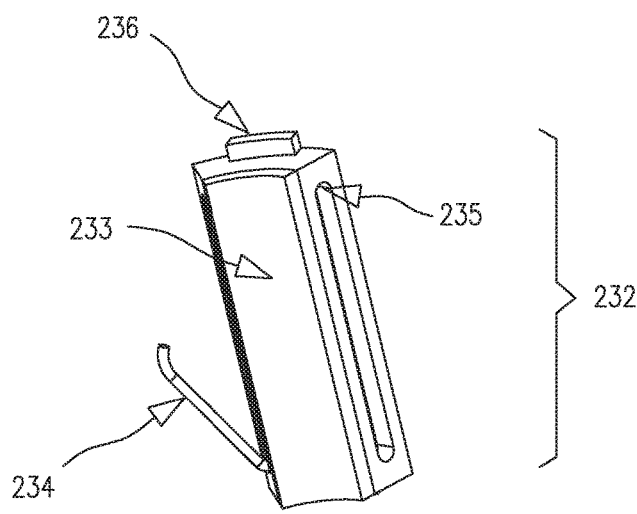
FIGS. 20A-C are schematic illustrations of a locking element, and housing therefor, in accordance with some applications of the present invention.
Figure 20B:
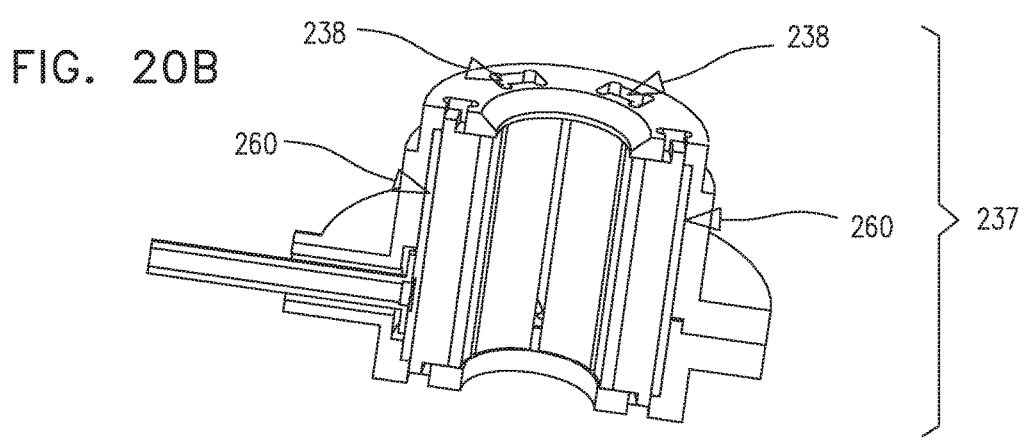
Figure 20C:
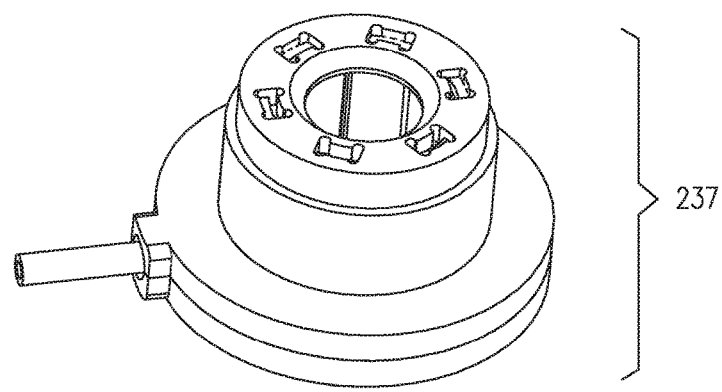
Figure 21A:
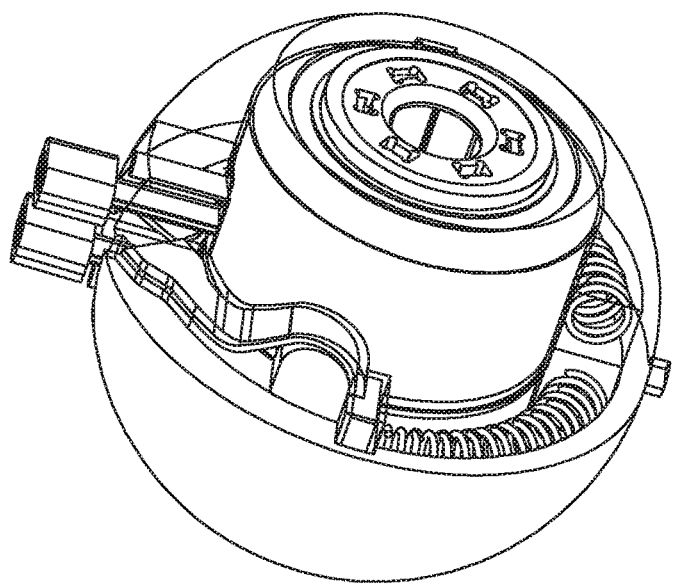
FIGS. 21A-B are schematic illustrations of a combined push/pull and rotation pneumatic stepper motor mechanism, in accordance with some applications of the present invention.
Figure 21B:
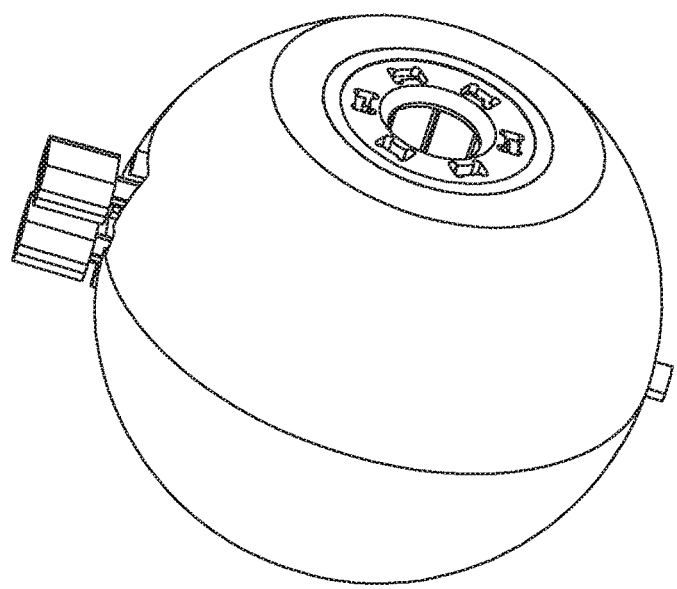

Reference is now made to FIGS. 20A-C and FIGS. 21A-B. FIG. 20A shows a locking element 232, a plurality of which can be used to surround circular shaft 240/340 (as shown in FIGS. 15A-B and 16). Locking element 232 typically comprises a high friction coating 233 and a rigid locking element body 235. Shown also is return spring 234. The top, and bottom (not shown), of locking element body 235 are shaped to define tabs 236 that fit into orifices 238 of the housing 237, shown in the cross-section in FIG. 20B. Tabs 236 generally restrict the motion of locking element 232 to radial motion, such that little or no shear forces are applied to locking balloon 260. Though FIGS. 20B-C show an application in which there are six locking elements, the number of locking elements can be greater or less than six. In some applications, return spring 234 is a leaf spring, which acts to increase the distance between locking elements 232 when locking balloon 260 is deflated. FIG. 20C shows a fuller view of housing 237. FIGS. 21A-B show the combined push/pull and rotation pneumatic stepper motor mechanism of FIG. 17, with the addition of locking elements 232.

Remote Surgery

Figure 23:
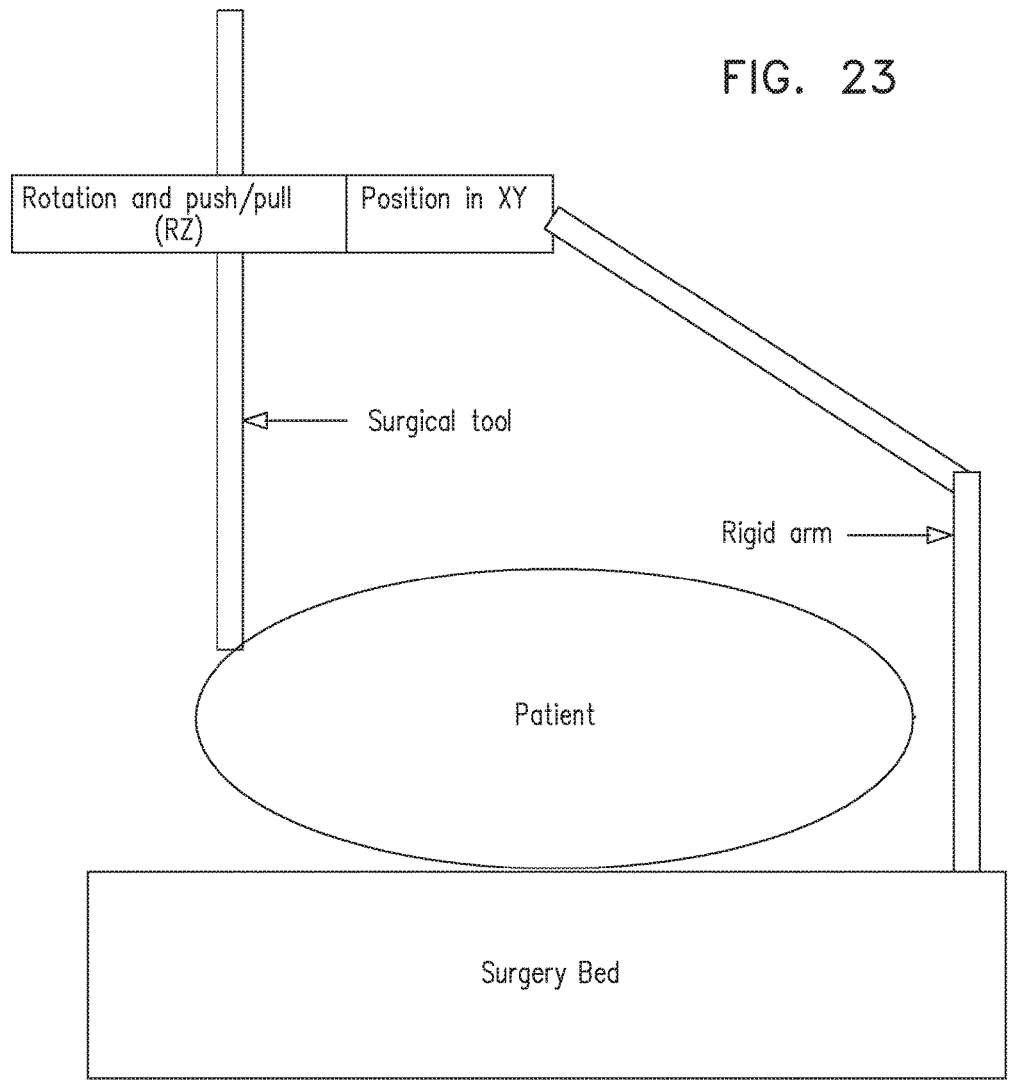
FIG. 23 is a schematic illustration of the operation of a surgical tool, in accordance with some applications of the present invention.

Pneumatic tool operation, using mechanisms of pneumatic control of X/Y position, shaft rotation, and shaft in/out motion, as described hereinabove, typically provides full control of minimally-invasive surgical tools and laparoscopes, e.g., as schematically illustrated in FIG. 23. In addition to the four motion degrees of freedom (DOF) described herein, the operation of a tool handle provides a fifth degree of freedom. Control of the five degrees of freedom can be either by a nearby surgeon or a remote surgeon, facilitating inexpensive robotic capabilities and remote surgery.

The use of pneumatic, balloon based, motors as described herein allows for the design of disposable motion mechanisms driven remotely by pneumatic lines. The pneumatic control system—valves, gauges, regulators—can be all removed from the motion mechanism, keeping the moving parts compact and inexpensive. Specifically in hospital environments, the pneumatic motors can use the existing hospital air pressure systems without the use of additional air compressors.

Reference is again made to FIGS. 14A-B. FIGS. 14A-B show two views for optional integration of four degrees of freedom motion mechanism based on balloon-operated pneumatic stepper motors described herein. The mechanism includes combined X and Y slides and combined rotation and push/pull motors (in the ball) for a total of four degrees of freedom. Adding to this unit another mechanism for tool opening/closing (e.g., as described herein) provides a fifth degree of freedom resulting in full control over a laparoscopic surgery tool.

Articulated Tool Operation

The use of MIS tools having articulation capabilities, for example, being able to bend at, and change direction of, the distal end, is important in some complex surgery tasks such as suturing. The control of the articulated tool end using two additional Degrees Of Freedom (DOF), however, adds complexity and cognitive load to the manipulation of the tool by the surgeon. Reducing the complexity is useful for wide acceptance of articulated tools in MIS. Applications of the present invention include various options to use robotic control, and specifically pneumatic robotic control, to enhance articulated tool operation.

Pneumatic Articulation Control

Balloon-based pneumatic operation (e.g., as described herein) can be used for the control of MIS tool articulation, either directly or indirectly. Adding four low-profile balloons to a mechanical articulation joint allows direct bending in any degree and angle. The pneumatic lines in this case may transverse the tool shaft to reach the balloon location. Pneumatic motors can be used for indirect control of articulation, by operating mechanical levers or pulleys that directly control the tool articulation, in a similar manner to the use of a pushrod for operation of an MIS tool handle.

Temporary Locking of Selected Degrees of Freedom (DOF)

An MIS tool held in a pneumatic robotic motion control unit can be quickly and easily made 'locked' in position (by inflating 'locking' balloons) and unlocked (by deflating 'locking' balloons), as described herein. This property allows the surgeon to temporarily 'lock' a selected Degree Of Freedom (DOF), for example, XYZ motion and/or shaft rotation and concentrate on manipulation of only the articulation DOF (bending, rotation). Similarly, the articulation DOF can be 'locked' while other DOF are manipulated. The cognitive load and motion complexity are both thereby reduced, allowing better use of the capabilities of articulated MIS tools. For placing the tool in a desired position, without significant resistance, all DOF's can be simultaneously released, and 'locked' again subsequent to placement.

Gaze Control for Articulation

An aspect of the system described herein (with reference to FIG. 2) includes the use of surgeon gaze control for automatic laparoscope motion. The pneumatic motion systems described herein are configured to move the laparoscope to follow the surgeon's gaze, automatically centering the displayed image obtained by the laparoscope. A variation of the gaze control system can be used for automatic manipulation of tool articulation. The gaze control system can switch from 'laparoscope control' to 'articulation control' mode, where the surgeon's gaze determines the location where the tool end should be by changing the articulation DOF. In this mode of operation, the surgeon controls the 'standard' DOF of the tool. A crosshair (or other cursor) is displayed on the screen showing the estimation of the surgeon gaze direction. The pneumatic system (or other automatic control system) is used to control the articulation of the chosen MIS tool so as to bring the tool tip to the crosshair location on the display. Use of a 3D display and 3D crosshair gives 3D control of tool articulation. The surgeon may switch the 'articulation control' mode on or off according to need. Software for tracking the MIS tool in the image can be used to determine the amount and direction of the desired articulation motion.

Small Footprint R/Theta Motion Stage

Figure 22:
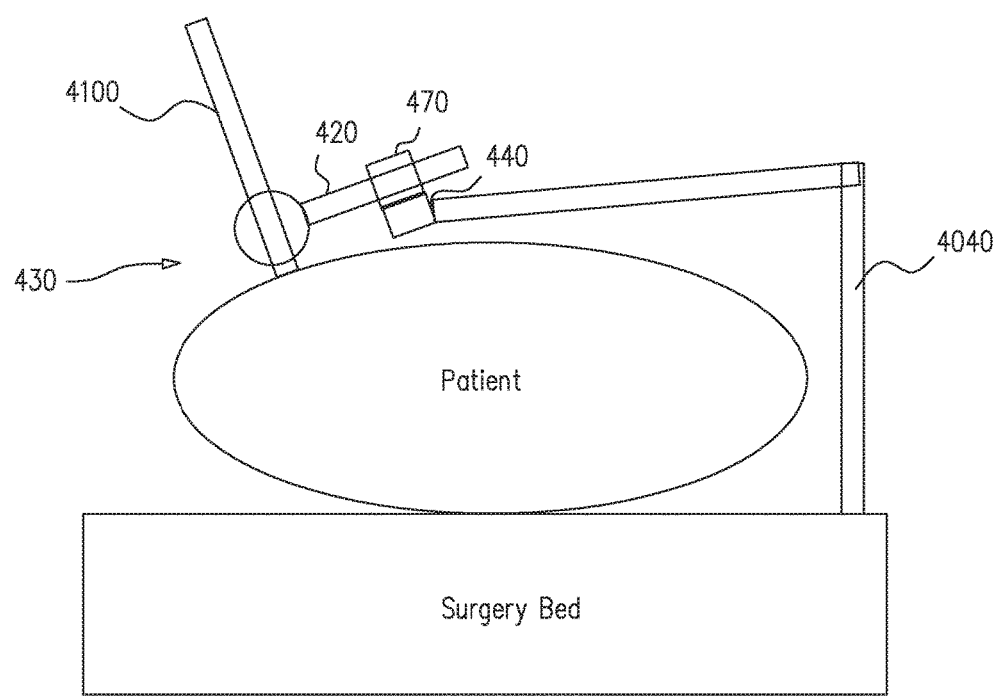
FIG. 22 is a schematic illustration of a surgical tool with four degrees of freedom, in accordance with some applications of the present invention.

In using pneumatic stepper motors for control of minimally invasive surgery tools, a small footprint near the entry point to the body is typically important, as the surgeon often wishes to place a few body entry points near each other. The use of the combination of linear and rotation motion—R/theta—instead of two perpendicular linear slides—X/Y—enables a smaller footprint near the body entry point. As FIG. 22 shows, this arrangement may be more natural for placement by the surgeon, since there are two fixed points in the clinical setup—the body entry point trocar and the rigid arm support position above the patient. The linear motion direction connects the two points and does not stray from this line.

FIG. 22 shows a combined Z/rotation balloon-operated motion stage 430, allowing moving of a surgical tool shaft 4100 in and out of the body, and rotation of the surgical tool shaft. A post 420 is connected to stage 430, and passes through a Z motion stage 410. Moving the post 420 through stage 410 will force a change of angle of the surgical tool in the plane of the figure. Motion stage 410 is connected to a rotation stage 440, rotating around an axis in the plane of the figure (parallel to the tool shaft in this figure). Rotation of stage 440 will force a change of angle of post 420 out of the plane of the figure, and a corresponding change of angle of the tool shaft. Overall, the arrangement depicted in FIG. 22 provides four degrees of freedom control of the surgical tool (three rotation angles, in and out motion) in a small footprint arrangement.

An alternative arrangement for a small footprint near the trocar is to connect two rotation stages with fixed length posts (similar to the rigid arm 4040 two-post setup shown in FIG. 22), such that rotation of both stages moves motion stage 430 and covers the same motion range as X/Y or R/theta arrangements.

It will be apparent to those of skill in the art that there exist many alternative combinations of X, Y, Z, and rotation stages that can be used to enable the desired control and freedom of movement of the surgical tool. For example, one such alternative combination, allowing for the same range of motion as an XY stage, comprises two rotation stages attached to each other by links.

Combination Trocar and Pneumatic Motion Stage

FIG. 22 shows surgical tool 4100 passing through motion stage 430 and entering the patient's body through an entry point, e.g., through a trocar. Disposable trocars are becoming standard in modern hospitals, since they reduce risk of contamination and sterilization costs. The low cost design of balloon-based motion stages such as stages 430 and 410 allows for disposable combinations of a trocar with one or more motion stages. Such compact combinations would allow for quicker and more efficient surgeries.

Reference is made to FIGS. 1-26. Described hereinbelow are parameters of timing, motor speed, motion measurements, force, and balloon material parameters, for the pneumatic motors disclosed herein.

Timing Parameters

Surgical control apparatus, as described hereinabove with reference to FIGS. 1-26, typically comprises a pneumatic motor having a motor mechanism with inflatable balloons. The apparatus is typically operated in combination with a pressure source and further comprises control valves 1090 and tubes 1080 that connect the pressure source and the valves to the motor mechanism (as shown in FIG. 26). The valves are typically part of a multi-use control unit, while the motor mechanism and the tubes can be single-use and disposable.

Timing of a single motor motion step typically depends on a) valve operation times (open/close), b) pressure propagation time in the tubes, and c) balloon inflation/deflation times.

The following times and parameters are described by way of illustration and not limitation to provide typical timing of a single motor motion step:

a) Valve operation times: Fast switching commercially available pneumatic valves have switching times of 2-3 ms (for example, pneumatic valves from the MH2 solenoid valve series, manufactured by Festo Corporation).

b) Pressure propagation time in the tubes: tubing length is typically 0.1 to 3 meters. Since the sound velocity in air is around 330 m/s, pressure propagation time in the tubes varies from 0.3 ms for short, 10 cm, tubes to 10 ms for longer 3 meter tubes.

c) Balloon inflation and deflation times: these typically vary depending on a volume of the balloon and a size of the tube leading to it, which determines the maximum flow. Provided by example are, a small size balloon of 10 mm×10 mm×1 mm, or volume of 1000 mm3, and a tube with 1 mm2 cross section area (1.1 mm internal diameter). The theoretical maximum flow rate at the speed of sound will be 330 mm3/ms, or 0.3 ms for full inflation/deflation of the balloon. Realistic flow rates are typically not more than ⅓ of this rate, giving approximately 1 ms inflation and deflation times (or, more generally, 0.3-15 ms or 15-30 ms inflation and deflation times. It is noted that flow rate and inflation and deflation times may be longer.

Overall time for a single balloon operation is calculated by the sum of the valve operation time, pressure propagation time, and balloon inflation/deflation times, which add up to a typical minimum of 3 ms, and typically to 5-10 ms.

A single motor motion step typically requires three (3) single balloon operations, which may overlap, (e.g., inflation of one locking balloon, deflation of an opposite locking balloon, and inflation of a moving balloon) and takes typically 5 ms to 30 ms.

It is noted that these times are dependent on the distance between the control valves and the pneumatic motor; larger distances between the control valves and the pneumatic motor mechanism typically delay pressure propagation in the tubes, resulting in slower motor operation.

Motor Speed

The size of a single motor motion step is typically determined by mechanical design, and is typically between 0.1 mm to 1 mm. A single motion step typically takes approximately 10 ms (generally, 3-30 ms), and the resulting motor speed is typically limited to approximately 10 mm/s (generally, 3-30 mm/s) for a motion step size of 0.1 mm (generally, 0.03-0.3 mm), or 100 mm/s (generally, 30-300 mm/s) for a motion step size of 1 mm (generally, 0.3-3 mm).

Figure 25:
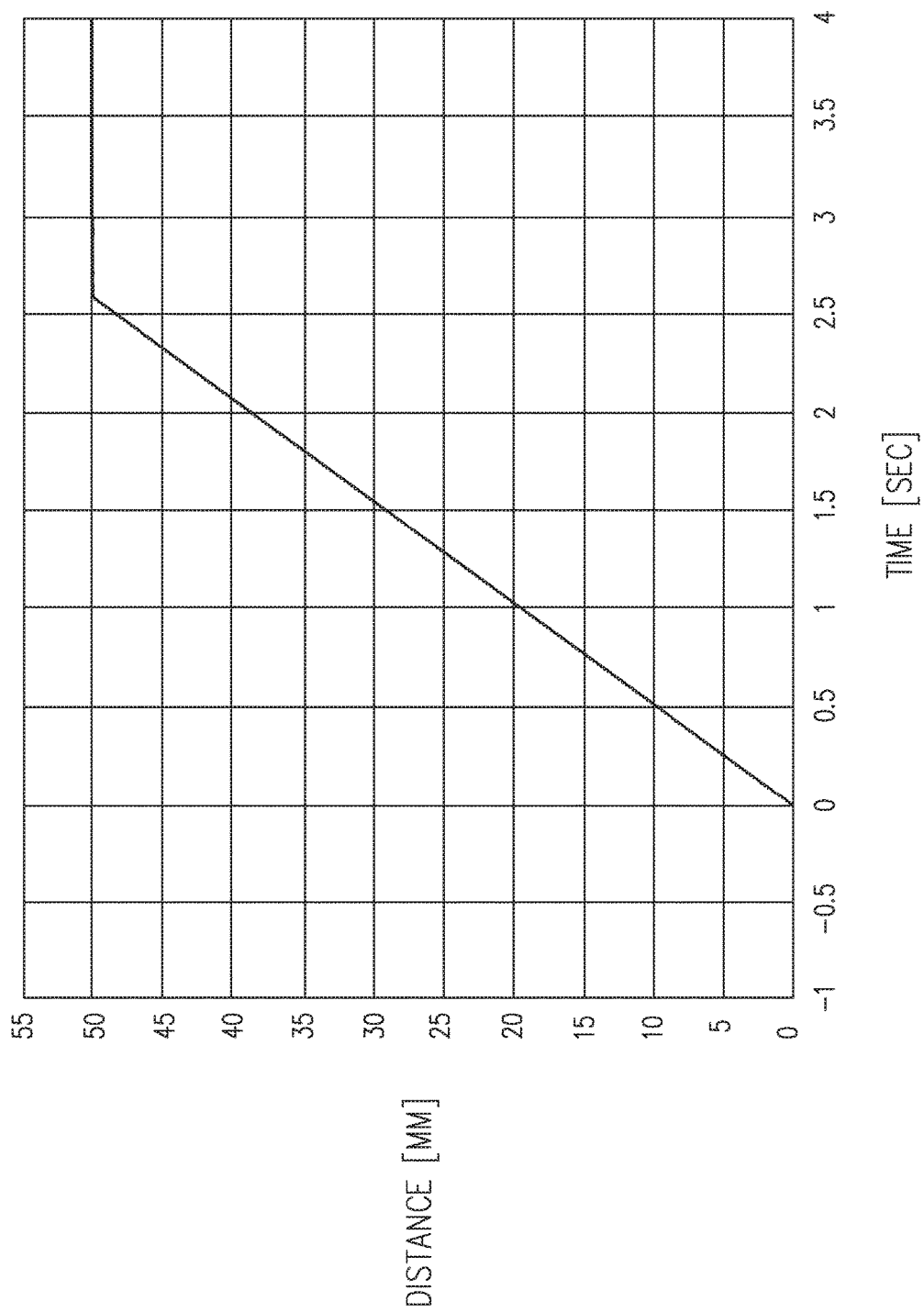
FIG. 25 is a graph representing motion measurement of a pneumatic linear motor, derived in accordance with some applications of the present invention.
Figure 26:
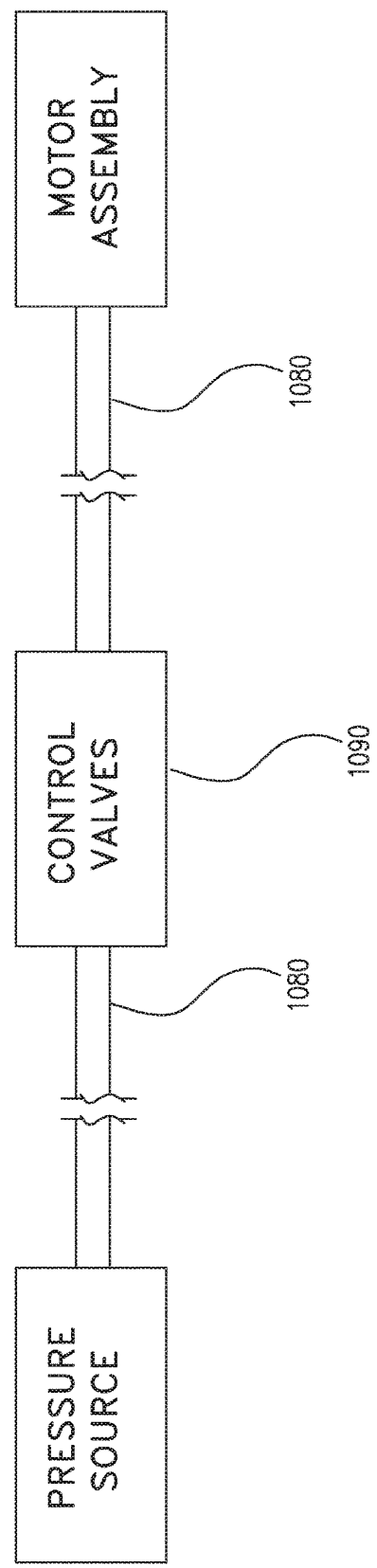
FIG. 26 is a block diagram of components for use with a pneumatic motor, in accordance with some applications of the present invention.

FIG. 25 shows a graph representing measured motion of a pneumatic linear motor built using the techniques described hereinabove, using a motion step size of 0.5 mm. The total motion distance is 50 mm, and motion velocity was about 19 mm/sec.

Force

The typical outlet pressure for a pneumatic motor is atmospheric pressure, i.e., 1 Atm. Operation pressure typically varies between 2 Atm to 20 Atm, depending on the forces to be produced by the motor. A typical balloon with an area of 1 cm2 (size 10 mm×10 mm) will exert a force of 10 kgF at a pressure of 10 Atm. The combined holding force of two balloons (two sides of a motor) is then 20 kgF.

Dynamic force carrying capacity, e.g., moving the motor to lift a weight, depends on the required velocity, operating pressure, and force of return springs in the mechanism. Using a return spring of 2 kgF, operating pressure of 5 Atm, and 1 cm2 balloon, typically yields a 2 Kg load lifting capacity.

Balloon Material Parameters

The main requirements of the balloon material are elasticity, medical compatibility, and industrial processing compatibility. A common medical grade material is Polyurethane. Polyether-based Thermoplastic Polyurethane (TPU) is available in both sheets and tubes, and is compatible with standard industrial processing methods such as heat processing and welding, and Radio Frequency (RF) welding. Typical TPU material is between 80 A to 90 A Shore hardness.

The wall thickness of the balloons can be thin, since the balloons are confined between external walls that limit the balloon expansion (e.g., locking element 132 and anchoring elements 120). There is a preference for thin balloon walls, as long as there are no 'folds' in the balloon construction. For a typical balloon size of 10 mm×10 mm, typical wall thickness is 0.1 mm (from 0.05 mm to 0.15 mm).

The tubing connection to the balloon typically has a tube cross section of 0.5 mm2 to 1.5 mm2, a tube internal diameter of 0.8 mm to 1.4 mm, and a tube external diameter of 1.3 mm to 2 mm (wall thickness about 0.3 mm).

Reference is made to FIGS. 1-26. It is noted, that the robotic surgical control apparatus described herein are configured for assisting any type of minimally-invasive surgery, e.g., and not only laparoscopic surgery.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Surgical pneumatic motor apparatus, comprising:
   first and second rails; and
   a pneumatic motor assembly, comprising:
      a first motor subassembly, comprising:
         a first-motor subassembly locking balloon, configured to lock the first rail to the first motor subassembly by inflation of the first-motor subassembly locking balloon; and
         a first-motor subassembly moving balloon, configured to move the first rail by a mechanism selected from the group consisting of:
            a) inflation of the first-motor subassembly moving balloon, when the first-motor subassembly locking balloon is inflated, and
            b) deflation of the first-motor subassembly moving balloon, when the first-motor subassembly locking balloon is inflated; and
      a second motor subassembly, comprising:
         a second-motor subassembly locking balloon, configured to lock the second rail to the second motor subassembly by inflation of the second-motor subassembly locking balloon; and
         a second-motor subassembly moving balloon, configured to move the second rail by a mechanism selected from the group consisting of:
            a) inflation of the second-motor subassembly moving balloon, when the second-motor subassembly locking balloon is inflated, and
            b) deflation of the second-motor subassembly moving balloon, when the second-motor subassembly locking balloon is inflated.

2. The apparatus according to claim 1, wherein:
   the first motor subassembly further comprises a first-motor subassembly spring, configured to oppose motion induced by inflation of the first-motor subassembly moving balloon, and
   the second motor subassembly further comprises a second-motor subassembly spring, configured to oppose motion induced by inflation of the second-motor subassembly moving balloon.

3. The apparatus according to claim 1, wherein the first-motor subassembly moving balloon is configured to move the first rail in a first direction by inflation of the first-motor subassembly moving balloon, when the first-motor subassembly locking balloon is inflated, and wherein the second-motor subassembly moving balloon is configured to move the second rail in the first direction by deflation of the second-motor subassembly moving balloon, when the second-motor subassembly locking balloon is inflated.

4. The apparatus according to claim 1, wherein the first-motor subassembly moving balloon is configured to move the first rail in a first direction by inflation of the first-motor subassembly moving balloon, when the first-motor subassembly locking balloon is inflated, and wherein the second-motor subassembly moving balloon is configured to move the second rail in the first direction by inflation of the second-motor subassembly moving balloon, when the second-motor subassembly locking balloon is inflated.

5. The apparatus according to claim 1, wherein:
   the first motor subassembly further comprises a first-motor subassembly locking element,
   the first-motor subassembly locking balloon is configured to lock the first rail to the first motor subassembly by pushing the first-motor subassembly locking element against the first rail,
   the second motor subassembly further comprises a second-motor subassembly locking element, and
   the second-motor subassembly locking balloon is configured to lock the second rail to the second motor subassembly by pushing the second-motor subassembly locking element against the second rail.

6. The apparatus according to claim 5, further comprising a first and a second motor subassembly spring positioned to compress the first-motor subassembly locking balloon and second-motor subassembly locking balloon, respectively, by applying respective forces to the first-motor subassembly locking element and to the second-motor subassembly locking element.

7. The apparatus according to claim 5, wherein the first motor subassembly is shaped to define a restricting wall, configured to only allow motion of the first-motor subassembly locking element that is toward the first rail or away from the first rail.

8. The apparatus according to claim 5, wherein the second motor subassembly is shaped to define a restricting wall, configured to only allow motion of the second-motor subassembly locking element that is toward the second rail or away from the second rail.

9. The apparatus according to claim 5,
wherein the first-motor subassembly locking element is configured to prevent inflation of the first-motor subassembly locking balloon to a maximum inflation volume thereof, and
wherein the second-motor subassembly locking element is configured to prevent inflation of the second-motor subassembly locking balloon to a maximum inflation volume thereof.

10. The apparatus according to claim 1, wherein the first-motor subassembly locking balloon is configured to lock the first rail to the first motor subassembly by applying a force of 5-15 kgF.

11. The apparatus according to claim 1, wherein the subassembly locking balloons each have a volume of 10-200 mm3 when fully inflated.

12. The apparatus according to claim 1, wherein the first-motor subassembly moving balloon and the second-motor subassembly moving balloon are configured to move the first and second rails during motion steps having a time duration of 10-30 ms.

13. The apparatus according to claim 1, wherein the first-motor subassembly moving balloon and the second-motor subassembly moving balloon are configured to move the first and second rails by 0.1-1 mm during respective motion steps.

14. The apparatus according to claim 1, wherein the first-motor subassembly locking balloon and the second-motor subassembly locking balloon each has a wall thickness of 0.05 mm to 0.15 mm.

15. The apparatus according to claim 1, wherein the first-motor subassembly moving balloon and the second-motor subassembly moving balloon each has a wall thickness of 0.05 mm to 0.15 mm.

16. Surgical pneumatic motor apparatus for use with a shaft, comprising:
a pneumatic motor assembly, comprising:
a first motor subassembly, comprising:
a first-motor subassembly locking balloon, configured to lock the shaft to the first motor subassembly by inflation of the first-motor subassembly locking balloon; and
a first-motor subassembly moving balloon, configured to move the shaft by a mechanism selected from the group consisting of:
a) inflation of the first-motor subassembly moving balloon, when the first-motor subassembly locking balloon is inflated, and
b) deflation of the first-motor subassembly moving balloon, when the first-motor subassembly locking balloon is inflated; and
a second motor subassembly, comprising:
a second-motor subassembly locking balloon, configured to lock the shaft to the second motor subassembly by inflation of the second-motor subassembly locking balloon; and
a second-motor subassembly moving balloon, configured to move the shaft by a mechanism selected from the group consisting of:
a) inflation of the second-motor subassembly moving balloon, when the second-motor subassembly locking balloon is inflated, and
b) deflation of the second-motor subassembly moving balloon, when the second-motor subassembly locking balloon is inflated.

17. The apparatus according to claim 16, wherein the first-motor subassembly moving balloon and the second-motor subassembly moving balloon are configured to move the shaft by moving the shaft along a longitudinal axis thereof.

18. The apparatus according to claim 16, wherein the first-motor subassembly moving balloon is configured to move the shaft in a first direction by inflation of the first-motor subassembly moving balloon, when the first-motor subassembly locking balloon is inflated, and wherein the second-motor subassembly moving balloon is configured to move the shaft in the first direction by deflation of the second-motor subassembly moving balloon, when the second-motor subassembly locking balloon is inflated.

19. The apparatus according to claim 16, wherein the first-motor subassembly moving balloon is configured to move the shaft in a first direction by inflation of the first-motor subassembly moving balloon, when the first-motor subassembly locking balloon is inflated, and wherein the second-motor subassembly moving balloon is configured to move the shaft in the first direction by inflation of the second-motor subassembly moving balloon, when the second-motor subassembly locking balloon is inflated.

20. The apparatus according to claim 16, wherein:
the first motor further comprises a first-motor subassembly locking element,
the first-motor subassembly locking balloon is configured to lock the shaft to the first motor by pushing the first-motor subassembly locking element against the shaft,
the second motor subassembly further comprises a second-motor subassembly locking element, and
the second-motor subassembly locking balloon is configured to lock the shaft to the second motor subassembly by pushing the second-motor locking element against the shaft.

21. The apparatus according to claim 16, wherein:
the first motor subassembly further comprises a first-motor subassembly spring, configured to oppose motion induced by inflation of the first-motor subassembly moving balloon, and
the second motor subassembly further comprises a second-motor subassembly spring, configured to oppose motion induced by inflation of the second-motor subassembly moving balloon.

22. The apparatus according to claim 16, wherein the first-motor subassembly moving balloon and the second-motor subassembly moving balloon are configured to move the shaft by rotation of the shaft.

23. The apparatus according to claim 22, wherein the first-motor subassembly locking balloon is configured to surround the shaft, and wherein the second-motor subassembly locking balloon is configured to surround the shaft.

* * * * *